US011532240B2

United States Patent
Johnson et al.

(10) Patent No.: US 11,532,240 B2
(45) Date of Patent: Dec. 20, 2022

(54) AUDIO-ONLY INTERFERENCE TRAINING FOR COGNITIVE DISORDER SCREENING AND TREATMENT

(71) Applicant: Akili Interactive Labs, Inc., Boston, MA (US)

(72) Inventors: Jason Johnson, Novato, CA (US); Jason Trees, Dedham, MA (US); Elena Cañadas Espinosa, Dorchester, MA (US)

(73) Assignee: Akili Interactive Labs, Inc., Boston, MA (US)

( * ) Notice: Subject to any disclaimer, the term of this patent is extended or adjusted under 35 U.S.C. 154(b) by 0 days.

(21) Appl. No.: 17/316,511

(22) Filed: May 10, 2021

(65) Prior Publication Data
US 2022/0060830 A1 Feb. 24, 2022

Related U.S. Application Data

(63) Continuation of application No. PCT/US2019/061032, filed on Nov. 12, 2019.
(Continued)

(51) Int. Cl.
*G09B 5/04* (2006.01)
*H04S 1/00* (2006.01)
(Continued)

(52) U.S. Cl.
CPC ............ *G09B 5/04* (2013.01); *A61B 5/12* (2013.01); *G06F 3/165* (2013.01); *G06F 3/167* (2013.01);
(Continued)

(58) Field of Classification Search
None
See application file for complete search history.

(56) References Cited

U.S. PATENT DOCUMENTS

| 9,940,844 | B2 | 4/2018 | Gazzaley | |
| 2007/0293735 | A1* | 12/2007 | Chan | A61B 5/16 600/300 |

(Continued)

OTHER PUBLICATIONS

Draganova, Rossitza, et al., "Modulation of auditory evoked responses to spectral and temporal changes by behavioral discrimination training." BMC Neuroscience 2009, 10:143. BioMed Central. Online publication at https://bmcneurosci.biomedcentral.com/articles/10.1186/1471-2202-10-143.
(Continued)

*Primary Examiner* — Paul W Huber
(74) *Attorney, Agent, or Firm* — Gregory Finch; Finch Paolino, LLC

(57) ABSTRACT

Generating, rendering and outputting one or more audio signals that have one or more audio sequences and/or spectral modulations of an audio file including a plurality of audio-based user prompts in an audio interference processing system. An audio interference processing system and method incudes initiating an instance of an audio interference processing session, configuring one or more session parameters, rendering/outputting a training audio output to one or more transducers, rendering/outputting one or more audio discrimination and audio navigation signals to the one or more transducers, receiving two or more sensor inputs in response to rendering/outputting one or more audio discrimination and audio navigation signals to the one or more transducers, processing the two or more sensor inputs, and providing a feedback output to a user via one or more modalities.

20 Claims, 23 Drawing Sheets

Related U.S. Application Data

(60) Provisional application No. 62/758,464, filed on Nov. 9, 2018.

(51) Int. Cl.
  *G06F 3/16* (2006.01)
  *A61B 5/12* (2006.01)
  *H04R 5/033* (2006.01)
  *H04R 5/04* (2006.01)

(52) U.S. Cl.
  CPC ............... *H04R 5/033* (2013.01); *H04R 5/04* (2013.01); *H04S 1/007* (2013.01); *H04R 2499/11* (2013.01)

(56) References Cited

U.S. PATENT DOCUMENTS

| | | |
|---|---|---|
| 2011/0256513 A1 | 10/2011 | Levitt et al. |
| 2014/0352521 A1 | 12/2014 | Takahashi et al. |
| 2014/0370479 A1* | 12/2014 | Gazzaley ................ G09B 7/02 434/322 |
| 2015/0051508 A1 | 2/2015 | Ghajar et al. |
| 2016/0005320 A1* | 1/2016 | deCharms ............ A61B 8/0808 434/236 |
| 2017/0046971 A1 | 2/2017 | Moreno |
| 2017/0249855 A1* | 8/2017 | Gazzaley ............... G09B 19/00 |
| 2018/0133431 A1* | 5/2018 | Malchano .............. A61B 5/377 |

OTHER PUBLICATIONS

International Search Report, International application No. PCT/US2019/061032. dated Feb. 6, 2020. ISA/US, Alexandria, VA.

Written Opinion of the International Searching Authority, International application No. PCT/US2019/061032. dated Feb. 6, 2020. ISA/US, Alexandria, VA.

Extended European Search report, European application No. 19880977.4. dated Jun. 28, 2022. European Patent Office, Munich, DE.

\* cited by examiner

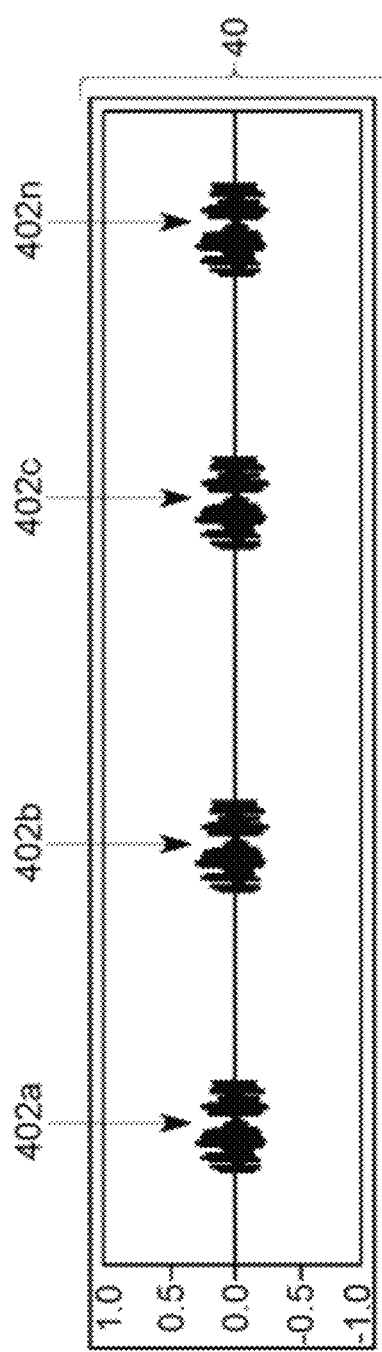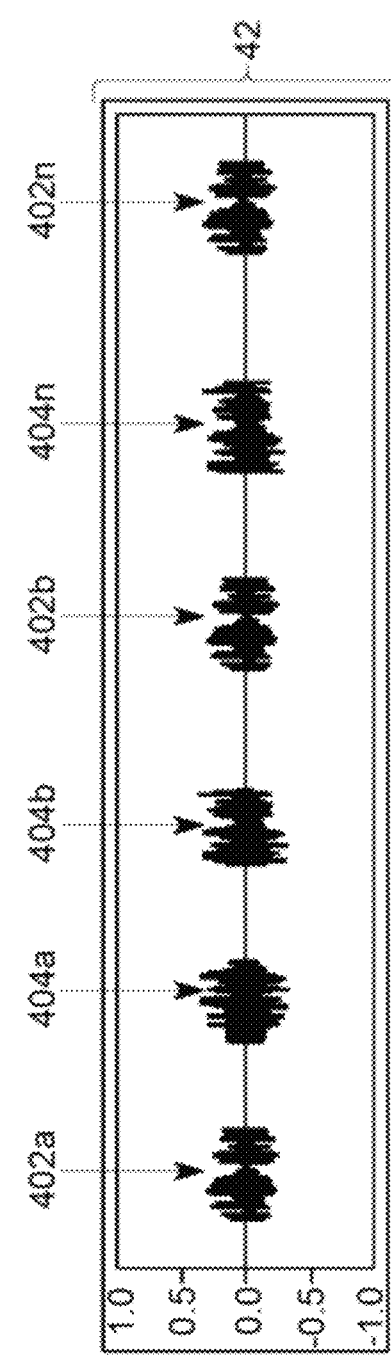

AUDIO-ONLY INTERFERENCE TRAINING FOR COGNITIVE DISORDER SCREENING AND TREATMENT

CROSS-REFERENCE TO RELATED APPLICATIONS

This application is a continuation of international application number PCT/US2019/061032 filed Nov. 12, 2019, which claims priority benefit of U.S. Provisional Application Ser. No. 62/758,464 filed Nov. 9, 2018; the entirety of each application is hereby incorporated herein at least by reference.

FIELD

The present disclosure relates to the field of computer-implemented diagnostic and therapeutic systems; in particular, an audio-only interference training system and method for the screening and treatment of cognitive disorders.

BACKGROUND

Cognitive decline and deficits are associated with a broad range of disorders, diseases and conditions, including decline related to normal aging, specific psychopathologies, and neurological disorders. Some cognitive deficits are related to processing of auditory and visual data, for example, and the command of motor functions while in an environment with challenging (noisy, time-limited, attentionally-demanding) conditions.

One deficit that distinguishes a neurotypical brain from a brain suffering from cognitive decline or a cognitive disease or disorder is the brain's ability to maintain cognitive performance in the presence of interrupting and distracting stimuli. Other deficits can involve the inability to multi-task and concentrate on performing a task in the presence of distractions.

Prior solutions have attempted to provide a variety of computer-implemented methods, systems and tools for improving cognitive ability in aging individuals, individuals suffering from cognitive impairment, or healthy individuals wishing to enhance their cognitive abilities according to a variety of methodologies. One such methodology is interference training, which seeks to employ various tasks and stimuli to improve an individual's ability to multi-task and concentrate on performing a task in the presence of distractions. For example, U.S. Pat. No. 9,940,844B2 to Gazzaley ("Gazzaley") provides for computer-implemented methods and tools for enhancing cognition in an individual by improving the individual's ability to deal with interference in cognitive function. Gazzaley provides for certain cognitive training methods involving presenting to an individual a task to be performed, presenting to the individual an interference, and receiving inputs from the individual. Where the interference is a distraction, the individual is to ignore the interference. Where the interference is an interrupter, the individual is instructed to respond to the interrupter as a secondary task, at which point the individual is said to be multi-tasking. Inputs are also received from the individual pertaining to this secondary task and include conducting an analysis of and/or generating feedback from the individual. The analysis includes a comparison of the performances with or without each type of interference, and, in some instances, the difficulty of the task is modulated as a function of this comparison.

Previous techniques for implementing interference training, such as those taught by Gazzaley, have depended on an audio-visual experience to drive a constant task and a target discrimination task. Such methods and systems are ill-suited for people who have physical impairments or difficulties, particularly visual impairment, or otherwise are subject to situations or conditions where they cannot effectively engage with a visual display.

Through applied effort, ingenuity, and innovation, Applicant has identified a number of deficiencies and problems with current systems, tools and methods for implementing interference training for improving one or more cognitive abilities in an individual. Applicant has developed a solution that is embodied by the present invention, embodiments of which are described in detail below.

SUMMARY

The following presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present certain exemplified embodiments of the invention in a simplified form as a prelude to the more detailed description that follows.

Certain aspects of the present disclosure provide for a computer-implemented method for audio interference processing, comprising presenting, with a processing unit, a first audio signal comprising an audio prompt for a first audio interference processing task, the first audio signal comprising a first signal sequence or a first modulation parameter; presenting, with the processing unit, a second audio signal comprising an audio prompt for a second audio interference processing task, the second audio signal comprising a second signal sequence or second modulation parameter; outputting, with an audio output device, each of the first audio signal and the second audio signal to the at least one audio output device at two or more periodic time points, wherein the two or more periodic time points comprise an instance of an audio interference processing session; receiving, with the processing unit, a first sensor input in response to outputting the first audio signal at the two or more time points; receiving, with the processing unit, a second sensor input in response to outputting the second audio signal at the two or more time points; and processing, with the processor, the first sensor input and the second sensor input according to at least one input parameter, the at least one input parameter comprising a timing parameter and a task parameter.

Certain embodiments of the present disclosure provide for an audio interference processing method wherein the first sensor input comprises an audio target discrimination input, wherein the first audio interference processing task is an audio target discrimination task.

Certain embodiments of the present disclosure provide for an audio interference processing method wherein the second sensor input comprises an audio navigation input, wherein the second audio interference processing task is an audio navigation task.

Certain embodiments of the audio interference processing method may further comprise presenting, with the processing unit, a third audio signal comprising an audio interference output in the instance of the audio interference processing session.

Certain embodiments of the audio interference processing method may further comprise modifying, with the processor, the at least one input parameter in response to processing the first sensor input and the second sensor input, according to at least one task performance parameter.

Certain embodiments of the audio interference processing method may further comprise modifying, with the processor, a first signal sequence or a first modulation parameter of the first audio signal in response to processing the first or second sensor input, according to at least one task performance parameter.

Certain embodiments of the audio interference processing method may further comprise modifying, with the processor, a second signal sequence or a second modulation parameter of the second audio signal in response to processing the first or second sensor input, according to at least one task performance parameter.

Certain embodiments of the present disclosure provide for an audio interference processing method wherein the first audio signal comprises a randomly generated audio sequence comprising a subject audio target.

Certain embodiments of the present disclosure provide for an audio interference processing method wherein the second sensor input comprises turning a mobile electronic device in a direction of the second audio signal in a stereo field.

Certain embodiments of the present disclosure provide for an audio interference processing method wherein the first audio signal comprises a randomly generated audio sequence comprising a subject audio target, and the second audio signal comprises a panning modulation comprising a directional audio prompt.

Further aspects of the present disclosure provide for a system for audio interference processing, comprising at least one audio output device comprising at least one speaker or headphones; a mobile electronic device comprising at least one sensor and being operably configured to provide an audio signal to the at least one audio output device; an integral or remote processor communicatively engaged with the mobile electronic device; and a non-transitory computer readable medium having instructions stored thereon that, when executed, cause the processor to perform one or more operations, the one or more operations comprising: rendering a first audio signal comprising an audio prompt for a first audio interference processing task, the first audio signal comprising a first signal sequence or first modulation parameter; rendering a second audio signal comprising an audio prompt for a second audio interference processing task, the second audio signal comprising a second signal sequence or second modulation parameter; outputting each of the first audio signal and the second audio signal to the at least one audio output device at two or more periodic time points, wherein the two or more periodic time points comprise an instance of an audio interference processing session; receiving a first sensor input in response to outputting the first audio signal at the two or more time points; receiving a second sensor input in response to outputting the second audio signal at the two or more time points; and processing the first sensor input and the second sensor input according to at least one input parameter, the at least one input parameter comprising a timing parameter and a task parameter.

Certain embodiments of the present disclosure provide for an audio interference processing system wherein the at least one sensor comprises at least one of a touch sensor and a motion sensor.

Certain embodiments of the audio interference processing system may further comprise one or more operations for causing the processor to generate the first audio signal and the second audio signal according to one or more audio processing modules comprising at least one of a random sequence generator and a modulator.

Certain embodiments of the audio interference processing system may further comprise one or more operations for causing the processor to render a third audio signal comprising an audio interference output in the instance of the audio interference processing session.

Certain embodiments of the audio interference processing system may further comprise one or more operations for causing the processor to modify the first signal sequence or first modulation parameter of the first audio signal in response to processing the first or second sensor input, according to at least one performance parameter.

Certain embodiments of the audio interference processing system may further comprise one or more operations for causing the processor to modify the second signal sequence or second modulation parameter of the second audio signal in response to processing the first or second sensor input, according to at least one performance parameter.

Certain embodiments of the present disclosure provide for an audio interference processing system wherein the second sensor input comprises turning the mobile electronic device in a direction of the first audio signal or the second audio signal in a stereo field.

Certain embodiments of the present disclosure provide for an audio interference processing system wherein the first modulation parameter or the second modulation parameter is a panning modulation comprising an audio navigation parameter.

Certain embodiments of the present disclosure provide for an audio interference processing system wherein the one or more operations further comprise providing a feedback signal to the mobile electronic device in response to processing the first sensor input or the second sensor input.

Certain embodiments of the present disclosure provide for an audio interference processing system wherein the first audio interference processing task comprises an audio target discrimination task and the second audio interference processing task comprises an audio navigation task.

Still further aspects of the present disclosure provide for a non-transitory computer-readable medium encoded with instructions for commanding one or more processors to execute operations of a method for audio interference processing, the operations comprising processing a first audio signal and a second audio signal according to one or more audio processing parameters, the one or more audio processing parameters comprising at least one of a sequencing parameter and a modulation parameter, wherein the first audio signal comprises an audio prompt for a first audio interference processing task and the second audio signal comprises a second prompt for a second audio interference processing task; outputting each of the first audio signal and the second audio signal to an audio output device at two or more time points, wherein the two or more time points comprise an instance of an audio interference processing session; receiving a first sensor input in response to outputting the first audio signal at the two or more time points; receiving a second sensor input in response to outputting the second audio signal at the two or more time points; and processing the first sensor input and the second sensor input according to at least one input parameter, the at least one input parameter comprising a timing parameter and a task parameter.

The foregoing has outlined rather broadly the more pertinent and important features of the present invention so that the detailed description of the invention that follows may be better understood and so that the present contribution to the art can be more fully appreciated. Additional features of the invention will be described hereinafter which form the subject of the claims of the invention. It should be appreciated by those skilled in the art that the conception and the disclosed specific methods and structures may be readily utilized as a basis for modifying or designing other structures for carrying out the same purposes of the present invention. It should be realized by those skilled in the art that such equivalent structures do not depart from the spirit and scope of the invention as set forth in the appended claims.

BRIEF DESCRIPTION OF DRAWINGS

The above and other objects, features and advantages of the present disclosure will be more apparent from the following detailed description taken in conjunction with the accompanying drawings, in which:

FIG. 4A is a time/amplitude illustration of a target audio sequence comprising a target audio training instance, in accordance with an embodiment of the present disclosure;

FIG. 4B is a time/amplitude illustration of a target audio sequence and a non-target audio sequence comprising an audio discrimination instance according to an embodiment of the present disclosure;

DETAILED DESCRIPTION

Figure 1:
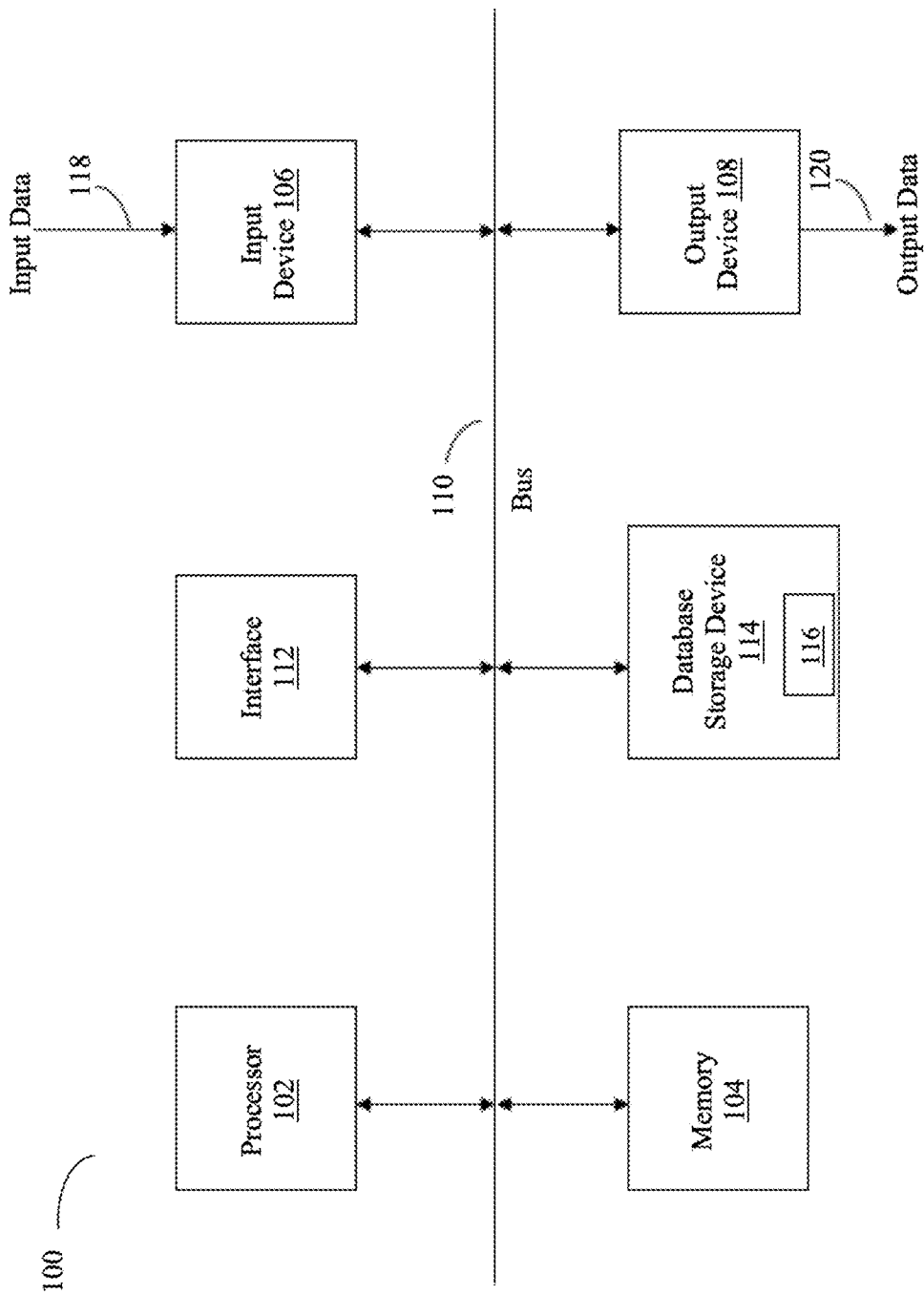
FIG. 1 is an illustrative embodiment of a computing device through which one or more aspects of the present disclosure may be implemented.

Turning now descriptively to the drawings, in which similar reference characters denote similar elements throughout the several views, FIG. 1 depicts a computing system in which certain illustrated embodiments of the present invention may be implemented.

Referring now to FIG. 1, a processor-implemented computing device in which one or more aspects of the present disclosure may be implemented is shown. According to an embodiment, a processing system 100 may generally comprise at least one processor 102, or a processing unit or plurality of processors, memory 104, at least one input device 106 and at least one output device 108, coupled together via a bus or a group of buses 110. In certain embodiments, input device 106 and output device 108 could be the same device. An interface 112 can also be provided for coupling the processing system 100 to one or more peripheral devices, for example interface 112 could be a PCI card or a PC card. At least one storage device 114 which houses at least one database 116 can also be provided. The memory 104 can be any form of memory device, for example, volatile or non-volatile memory, solid state storage devices, magnetic devices, etc. The processor 102 can comprise more than one distinct processing device, for example to handle different functions within the processing system 100. Input device 106 receives input data 118 and can comprise, for example, a keyboard, a pointer device such as a pen-like device or a mouse, audio receiving device for voice controlled activation such as a microphone, data receiver or antenna such as a modem or a wireless data adaptor, a data acquisition card, etc. Input data 118 can come from different sources, for example keyboard instructions in conjunction with data received via a network. Output device 108 produces or generates output data 120 and can comprise, for example, a display device or monitor in which case output data 120 is visual, a printer in which case output data 120 is printed, a port, such as for example a USB port, a peripheral component adaptor, a data transmitter or antenna such as a modem or wireless network adaptor, etc. Output data 120 can be distinct and/or derived from different output devices, for example a visual display on a monitor in conjunction with data transmitted to a network. A user could view data output, or an interpretation of the data output, on, for example, a monitor or using a printer. The storage device 114 can be any form of data or information storage means, for example, volatile or non-volatile memory, solid state storage devices, magnetic devices, etc.

In use, the processing system 100 is adapted to allow data or information to be stored in and/or retrieved from, via wired or wireless communication means, at least one database 116. The interface 112 may allow wired and/or wireless communication between the processing unit 102 and peripheral components that may serve a specialized purpose. In general, the processor 102 can receive instructions as input data 118 via input device 106 and can display processed results or other output to a user by utilizing output device 108. More than one input device 106 and/or output device 108 can be provided. It should be appreciated that the processing system 100 may be any form of terminal, server, specialized hardware, or the like.

It is to be appreciated that the processing system 100 may be a part of a networked communications system. Processing system 100 could connect to a network, for example the Internet or a WAN. Input data 118 and output data 120 can be communicated to other devices via the network. The transfer of information and/or data over the network can be achieved using wired communications means or wireless communications means. A server can facilitate the transfer of data between the network and one or more databases. A server and one or more database(s) provide an example of a suitable information source.

Thus, the processing computing system environment 100 illustrated in FIG. 1 may operate in a networked environment using logical connections to one or more remote computers. In embodiments, the remote computer may be a personal computer, a server, a router, a network PC, a peer device, or other common network node, and typically includes many or all of the elements described above.

It is to be further appreciated that the logical connections depicted in FIG. 1 include a local area network (LAN) and a wide area network (WAN), but may also include other networks such as a personal area network (PAN). Such networking environments are commonplace in offices, enterprise-wide computer networks, intranets, and the Internet. For instance, when used in a LAN networking environment, the computing system environment 100 is connected to the LAN through a network interface or adapter. When used in a WAN networking environment, the computing system environment typically includes a modem or other means for establishing communications over the WAN, such as the Internet. The modem, which may be internal or external, may be connected to a system bus via a user input interface, or via another appropriate mechanism. In a networked environment, program modules depicted relative to the computing system environment 100, or portions thereof, may be stored in a remote memory storage device. It is to be appreciated that the illustrated network connections of FIG. 1 are exemplary and other means of establishing a communications link between multiple computers may be used.

FIG. 1 is intended to provide a brief, general description of an illustrative and/or suitable exemplary environment in which embodiments of the invention may be implemented. That is, FIG. 1 is but an example of a suitable environment and is not intended to suggest any limitations as to the structure, scope of use, or functionality of embodiments of the present invention exemplified therein. A particular environment should not be interpreted as having any dependency or requirement relating to any one or a specific combination of components illustrated in an exemplified operating environment. For example, in certain instances, one or more elements of an environment may be deemed not necessary and omitted. In other instances, one or more other elements may be deemed necessary and added.

In the description that follows, certain embodiments may be described with reference to acts and symbolic representations of operations that are performed by one or more computing devices, such as the computing system environment 100 of FIG. 1. As such, it will be understood that such acts and operations, which are at times referred to as being computer-executed, include the manipulation by the processor of the computer of electrical signals representing data in a structured form. This manipulation transforms data or maintains it at locations in the memory system of the computer, which reconfigures or otherwise alters the operation of the computer in a manner that is conventionally understood by those skilled in the art. The data structures in which data is maintained are physical locations of the memory that have particular properties defined by the format of the data. However, while certain embodiments may be described in the foregoing context, the scope of the disclosure is not meant to be limiting thereto, as those of skill in the art will appreciate that the acts and operations described hereinafter may also be implemented in hardware.

Embodiments may be implemented with numerous other general-purpose or special-purpose computing devices and computing system environments or configurations. Examples of well-known computing systems, environments, and configurations that may be suitable for use with embodiments of the invention include, but are not limited to, personal computers, handheld or laptop devices, personal digital assistants, multiprocessor systems, microprocessor-based systems, set top boxes, programmable consumer electronics, networks, minicomputers, server computers, game server computers, web server computers, mainframe computers, and distributed computing environments that include any of the above systems or devices.

Embodiments may be described in a general context of computer-executable instructions, such as program modules, being executed by a computer. Generally, program modules include routines, programs, objects, components, data structures, etc., that perform particular tasks or implement particular abstract data types. An embodiment may also be practiced in a distributed computing environment where tasks are performed by remote processing devices that are linked through a communications network. In a distributed computing environment, program modules may be located in both local and remote computer storage media including memory storage devices.

With the exemplary computing system environment 100 of FIG. 1 being generally shown and discussed above, description will now turn towards illustrated embodiments of the present invention which generally relate to systems and methods for audio-only interference training for the screening and treatment of cognitive disorders. It is to be understood and appreciated that certain aspects of the methods described herein comprise initiating an instance of an audio interference processing session, configuring one or more session parameters, rendering/outputting a training audio output to one or more transducers, rendering/outputting one or more audio discrimination and audio navigation signals to the one or more transducers, receiving two or more sensor inputs in response to rendering/outputting one or more audio discrimination and audio navigation signals to the one or more transducers, processing the two or more sensor inputs, and providing a feedback output to a user via one or more modalities.

Before the present invention and specific exemplary embodiments of the invention are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed by the invention. The upper and lower limits of these smaller ranges may independently be included in the smaller ranges, and are also encompassed by the invention, subject to any specifically excluded limit in a stated range. Where a stated range includes one or both of the endpoint limits, ranges excluding either or both of those included endpoints are also included in the scope of the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, exemplary methods and materials are now described. All publications mentioned herein are incorporated herein by reference to disclose and describe the methods and/or materials in connection with which the publications are cited.

It must be noted that as used herein and in the appended claims, the singular forms "a", "an," and "the" include plural referents unless the context clearly dictates otherwise. Thus, for example, reference to "a stimulus" includes a plurality of such stimuli. Reference to "signal" includes reference to one or more signals, one or more sequences of signals, one or more representations of sound, whether stored or embodied in a digital file format or rendered as an acoustic output, and equivalents thereof known to those skilled in the art, and so forth.

Any publications discussed herein are provided solely for their disclosure prior to the filing date of the present application. Nothing herein is to be construed as an admission that the present invention is not entitled to antedate such publication by virtue of prior invention. Further, the dates of publication provided may differ from the actual publication dates which may need to be independently confirmed.

Figure 2:
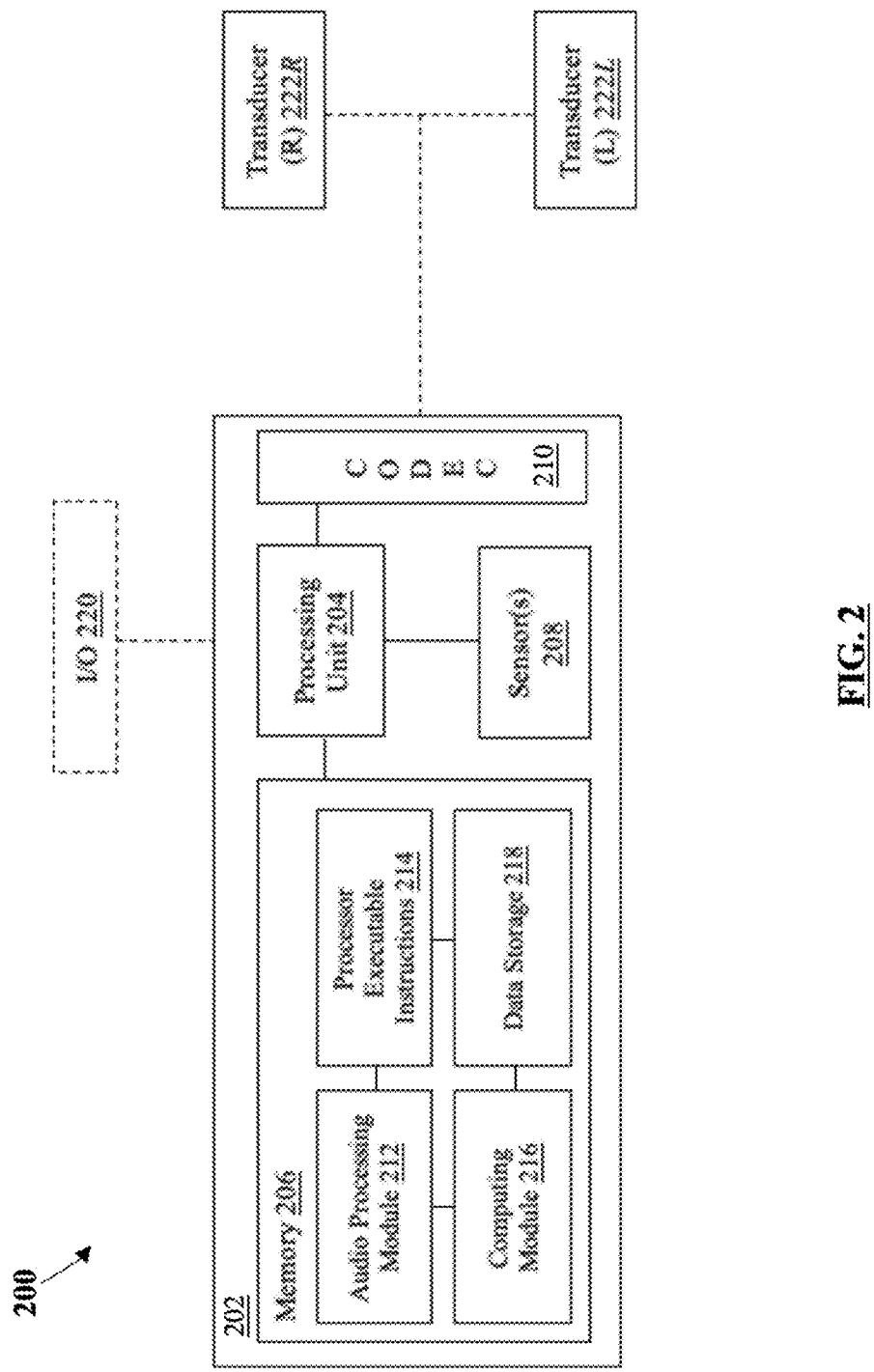
FIG. 2 is an illustrative embodiment of a computing system through which one or more aspects of the present disclosure may be implemented.

Referring now to FIG. 2, an illustrative embodiment of a computing system 200 through which one or more aspects of the present disclosure may be implemented is shown. In accordance with an embodiment, computing system 200 is comprised of a computing device 202 being communicably engaged with transducers 222R and 222L. In certain embodiments, computing device 202 is operably engaged with an input/output (I/O) device 220. Computing device 202 may be operably comprised of a processing unit 204, a memory 206, one or more sensors 208, and an audio codec 210. In certain embodiments, computing device 202 may be embodied as the exemplary computing system environment 100 of FIG. 1. Memory 206 may comprise a plurality of modules comprising instructions to cause processing unit 204 to perform certain functions and operations in accordance with an audio interference processing system and computer-implemented method. In accordance with an embodiment, memory 206 may comprise an audio processing module 212, processor executable instructions 214, a computing module 216, and data storage 218. Audio processing module 212 may comprise certain audio processing software that enables the processor to perform one or more audio processing functions. Audio processing module 212 may comprise one or more audio signal processing functions comprising an audio mixing function, an audio effects function, an audio rendering function, and an audio output function. Audio processing module 212 may comprise one or more software-based modulators comprising control parameters for manipulating one or more characteristics of a target signal or carrier, such as effects, spectral modulation, or sequencing. Audio processing module 212 may be configured to route a modulation source to modulate pitch, volume, pan, filter cutoff, wavetable index, and effects controls. In accordance with certain embodiments, one or more software-based modulators may comprise one or more of a low frequency oscillator, an ADSR envelope, a modulation wheel, and a step sequencer. Audio processing module 212 may comprise instructions for processing and rendering one or more audio sequences. In accordance with certain embodiments, an audio sequence may be generated through the application of a modulator function, such as a step sequencer module, or a signal generator function, such as a random sequence generator or MIDI generator. A step sequencer or signal generator function may comprise one or more control parameters that may be dynamically configured by computing module 216. Audio processing module 212 may comprise a spectral effects module configured to modulate the distribution of a sound signal in a stereo field and/or other spatial effects.

Computing module 216 may comprise application logic for executing an audio interference processing application on one or more computing devices. Computing module 216 may comprise instructions for controlling one or more audio processing functions of audio processing module 212, including instructions for dynamically controlling one or more audio processing functions. Computing module 216 may generally provide instructions for configuring one or more audio interference process controls, processing sensor inputs, and dynamically modifying one or more application or audio processing control parameters. Processor executable instructions 214 may be dynamically modified or informed by one or more control parameters of computing module 216, and may comprise instructions to enable processing unit 204 to execute a plurality of operations in an audio interference processing method, comprising initiating an instance of an audio interference processing session, rendering/outputting a training audio output to codec 210, rendering/outputting one or more audio discrimination and audio navigation signals to codec 210, receiving sensor inputs and user inputs from I/O device 220, processing the two or more sensor inputs and user inputs, and providing a feedback output to a user via I/O device 220 and/or other output modalities. Data storage 218 may be operable to store application controls, application data, and audio files, and may comprise one or more databases. Sensor(s) 208 may comprise one or more touch sensors or motion sensors, such as capacitive MEMS accelerometers, piezoresistive accelerometers, and piezoelectric accelerometers, gyroscope, e-compass, 5-wire (or 4-wire) resistive sensors, surface capacitive sensors, projected capacitive sensors, surface acoustic wave sensors, and infrared sensors, and the like. In certain embodiments, I/O device 220 may also comprise one or more touch sensors or motion sensors, such as those provided above.

Codec 210 may be a hardware audio codec operable to execute a digital-to-analog conversion of one or more audio discrimination and audio navigation signals and output to transducers 222R and 222L. In certain embodiment, codec 210 may be substituted for a digital-to-analog converter. Transducers 222R and 222L may comprise any type of acoustic transducer operable to output an acoustic soundwave. In certain embodiments, transducer 222R is embodied as a right speaker in a stereo field, and transducer 222L is embodied as a left speaker in a stereo sound field. In certain embodiments, transducers 222R and 222L are embodied as a pair of headphones. In other embodiments, computing system 200 may be comprised of a single transducer 222 in a monaural sound field. Alternatively, computing system 200 may be comprised of three or more transducers 222 operating in a stereophonic sound field between 180 and 360 degrees.

In certain embodiments, computing device 202 may comprise a smart phone or a tablet computer. In such embodiments, I/O device 220 may be configured as a touch screen display and integrally configured with computing device 202. I/O device 220 may further comprise an external input device, such as a mouse, joystick, gaming controller, and the like. I/O device 220 may be comprised of multiple input devices comprising multiple input modalities, such as one or more video cameras, microphones, wearable sensors, and touch screen interfaces; and, multiple output devices, such as one or more visual displays, audio speakers, and haptic output devices, such as wearable electronic devices. In certain embodiments, computing device 202 may be embodied in a completely audio-based format, such that I/O device 220 comprises one or more acoustic transducers comprising a microphone input and an audio speaker output.

Figure 3:
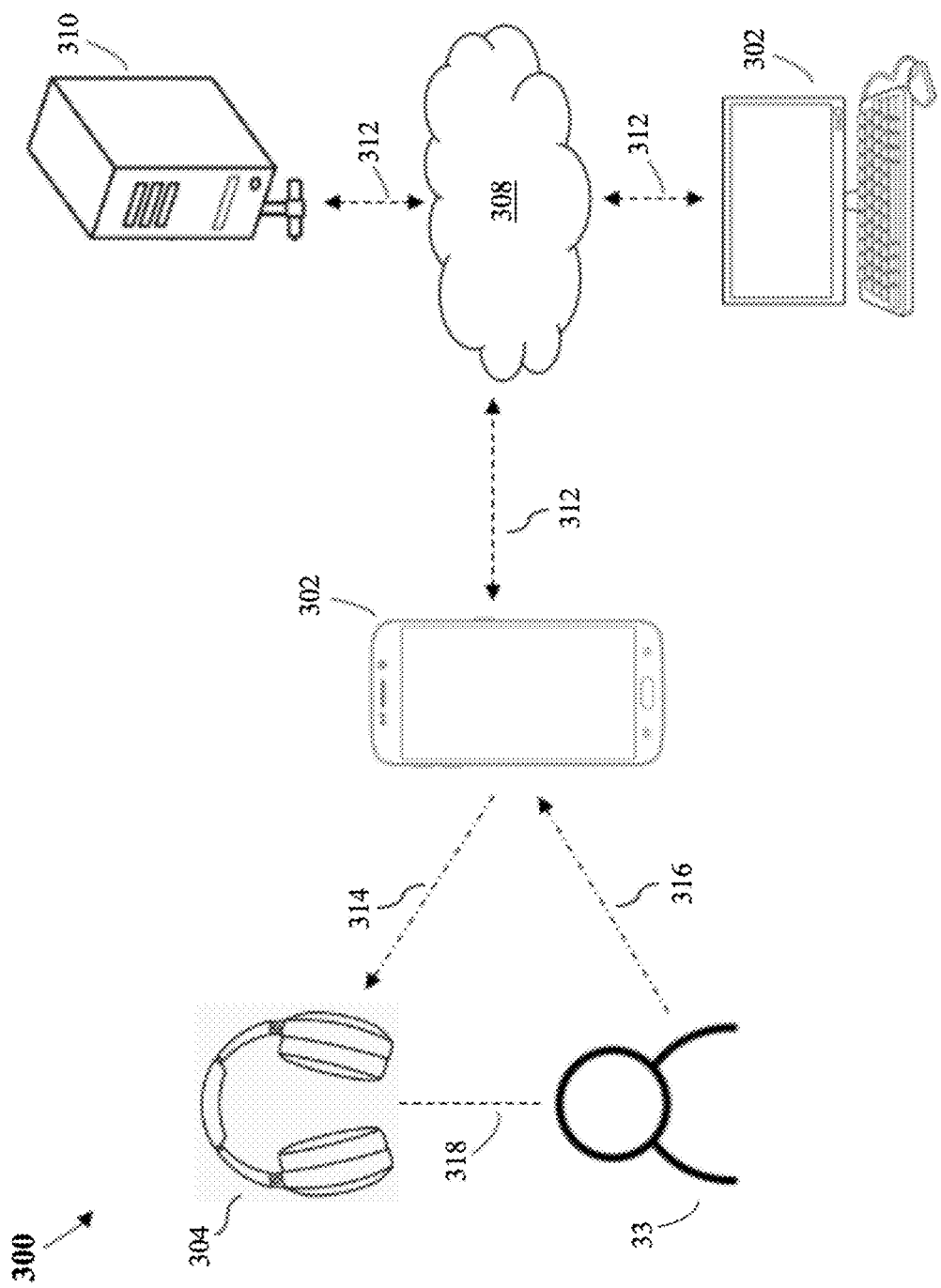
FIG. 3 is an illustrative embodiment of a system architecture through which one or more aspects of the present disclosure may be implemented.

Referring now to FIG. 3, an illustrative embodiment of a distributed computing environment 300 through which one or more aspects of the present disclosure may be implemented is shown. In accordance with an embodiment, an audio interference processing system is embodied in a distributed computing environment 300 comprising a mobile electronic device 302, a computing device 306, and one or more remote server 310. Mobile electronic device 302, computing device 306, and remote server 310 may be communicably engaged over a communications network 308 (e.g. the Internet) via a network interface 312 (e.g. an Internet connection). Each of the components, modules and functions of computing device 202, as shown and described in FIG. 2 above, may be distributed over one or more of mobile electronic device 302, computing device 306, and remote server 310. In accordance with certain embodiments, a user 33 executes an instance of an audio interference processing session by engaging with mobile electronic device 302 and headphones 304 to receive one or more audio prompts and execute one or more audio tasks. Mobile electronic device 302 may be communicably engaged with headphones 304 via a wireless or wireline communications interface 314 to provide one or more audio signals in accordance with an audio interference processing session. Headphones 304 may render an acoustic audio output 318 comprising one or more audio task prompts, audio interference(s) or distractor(s), and audio instructions. User 33 may provide a plurality of user inputs 316 to mobile electronic device 302 in response to audio output 318 via one or more input modalities, such as those described in FIG. 2 above. Mobile electronic device 302 may receive user inputs 316 and process user inputs 316 into one or more digital data format. Mobile electronic device 302 may perform subsequent processing steps to user inputs 316 and/or may communicate the digital data associated with user inputs 316 to computing device 306 and/or remote server 310 via communications interface 312.

Computing device 306 and/or remote server 310 may perform one or more data processing or analysis step(s) associated with an instance of an audio interference processing session and/or one or more data processing or analysis step(s) associated with an ongoing audio interference processing regimen. An audio interference processing regimen may comprise historical data, analysis, and application controls associated with multiple instances of audio interference processing sessions. Computing device 306 and/or remote server 310 may further comprise one or more HIPAA compliant data processing protocols for comparing and analyzing data across multiple users engaging in an audio interference processing regimen for the purpose of dynamically configuring one or more application controls or providing clinical or statistical insights to one or more healthcare practitioners, caregivers, insurers, and/or users. In certain embodiments, computing device 306 is associated with a user person other than the user engaging in the audio interference processing regimen, such as a healthcare practitioner, caregiver, insurer, and/or administrative user.

Remote server 310 may include one or more third-party application server(s), such as a media server for streaming music or otherwise accessing digital audio files.

Referring now to FIG. 4A, a time/amplitude diagram of an audio target 402 within an audio target training instance 40 is shown. An audio target 402 may be comprised of a repeating or characteristic sequence of notes, tones, effects, modulations, or other discernable audio characteristics. In accordance with an illustrative embodiment, an audio target 402 may comprise an audio sequence consisting of a two or three note/tone sequence being generated randomly from a set of three notes/tones. By means of illustration, the set of three notes may annotated as LOW, MEDIUM, and HIGH. An audio target 402 may be embodied as a randomly generated sequence such as LOW-LOW; LOW-HIGH; MEDIUM-HIGH; LOW-LOW-LOW; HIGH-MEDIUM-LOW; and other combinations. Audio target 402 may be presented to a user within an audio target training instance 40 wherein audio target 402 is repeated periodically as an audio output 402a-402n, such that a user can learn/memorize audio target 402.

Referring now to FIG. 4B, a time/amplitude diagram of audio target 402 and a non-target audio signal 404 comprising an audio target discrimination instance 42 is shown. In accordance with certain embodiments, audio target discrimination instance 42 comprises an audio output corresponding to an audio target discrimination task, a user is prompt to provide a user input corresponding to the user's ability to discriminate between audio target 402 and non-target audio signal 404 during audio target discrimination instance 42. In accordance with certain embodiments, non-target audio signal 404 may be comprised of a repeating or characteristic sequence of notes, tones, effects, modulations, or other discernable audio characteristics. Non-target audio signal 404 should comprise similar characteristics to that of audio target 402 such that a user may need to apply some degree of attention and cognition to discern between audio target 402 and non-target audio signal 404. In accordance with certain embodiments, non-target audio signal 404 may be comprised of an audio sequence consisting of the same set of notes/tones as audio target 402 but being arranged in a similar but distinct pattern. For example, if audio target 402 is comprised of the sequence: HIGH-MEDIUM-HIGH, then non-target audio signal 404 might be comprised of the sequence: HIGH-MEDIUM-LOW. A user may be periodically presented with one or more audio targets 402a-402n and one or more non-target audio signals 404a-404n at two or more time points comprising audio target discrimination instance 42.

Figure 4C:
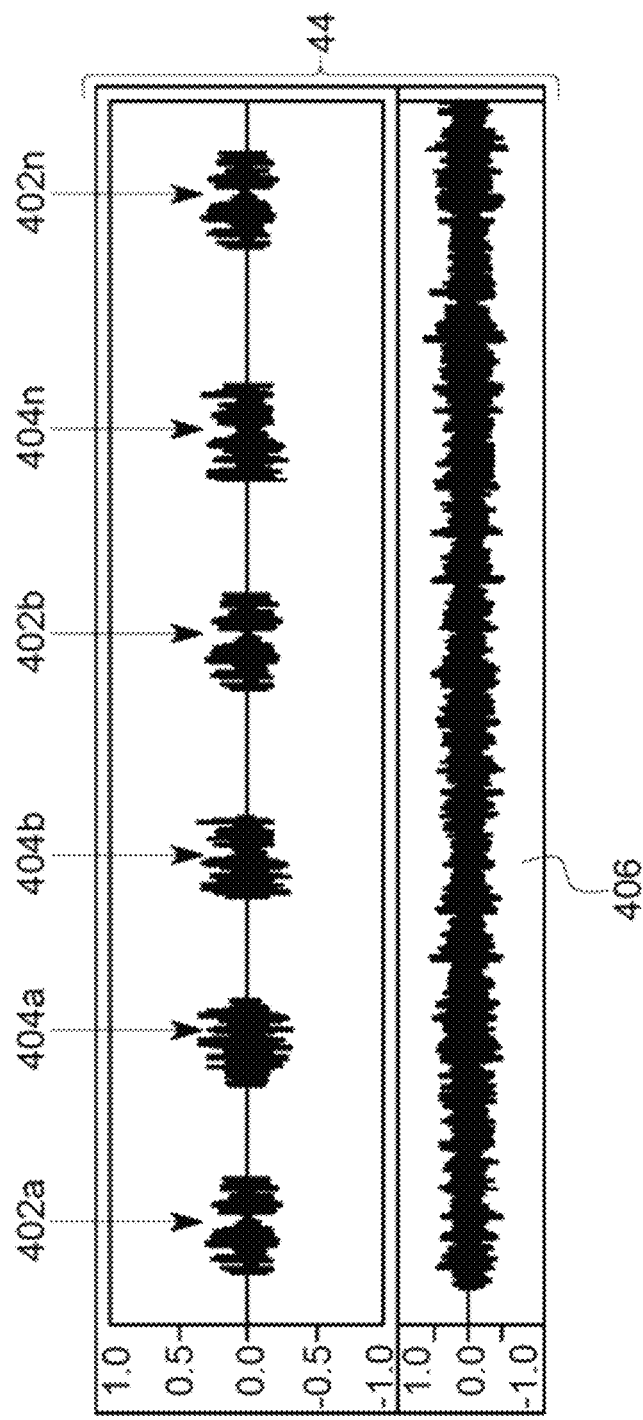
FIG. 4C is a time/amplitude illustration of a target audio sequence and a non-target audio sequence in the presence of a background audio file and comprising an audio discrimination instance, according to an embodiment of the present disclosure.

Referring now to FIG. 4C, a time/amplitude diagram of audio target 402 and a non-target audio signal 404 being presented in the presence of a background audio file 406 within an audio target discrimination instance 44 is shown. In accordance with certain embodiments, background audio file 406 may comprise a digital audio file comprising music or other recorded content, and/or may be comprised of one or more sequences of notes, tones, effects, modulations, or other audio characteristics. Background audio file 406 may comprise an interrupter or a distractor within audio target discrimination instance 44. For example, background audio file 406 may be configured as a song comprising certain audio characteristics being conducive to distraction, e.g. a fast, loud and/or instrumentally complex song. Audio target 402 and non-target audio signal 404 may be overlaid with background audio file 406 within an audio target discrimination instance 44. In certain embodiments, a time duration of background audio file 406 defines the time duration of audio target discrimination instance 44. For example, in certain illustrative embodiments audio target discrimination instance 44 comprises rendering an acoustic audio output comprising background audio file 406 (wherein background audio file 406 is optionally a song) and periodically presenting one or more audio targets 402a-402n and one or more non-target audio signals 404a-404n at two or more time points in the presence of background audio file 406.

Figure 5:
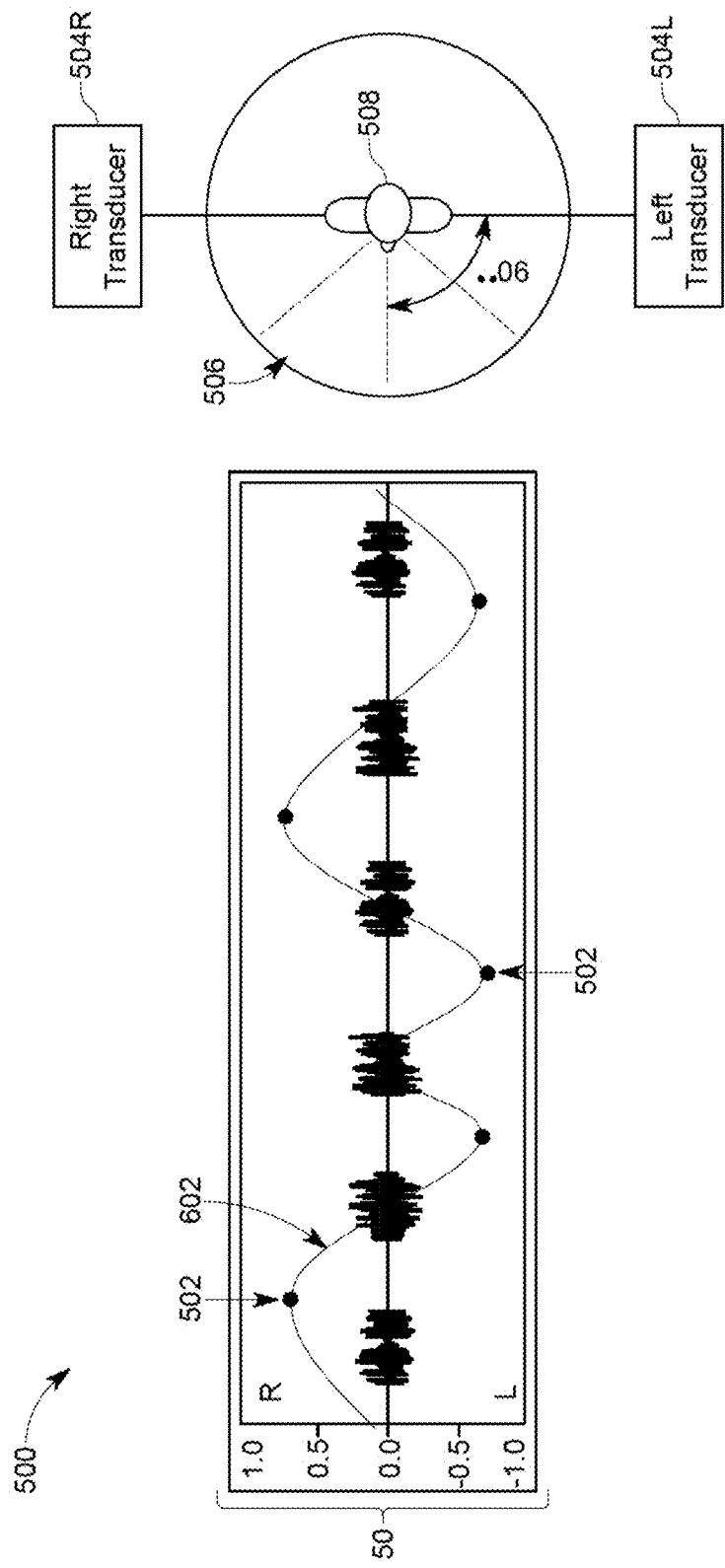
FIG. 5 is a time/amplitude illustration of a panning modulation for an audio output comprising an audio navigation instance, in accordance with an embodiment of the present disclosure.

Referring now to FIG. 5, a functional diagram 500 illustrating an audio navigation instance 50 comprising periodic presentment of an audio navigation signal 502 is shown. In accordance with certain embodiments, audio navigation instance 50 comprises an audio output corresponding to an audio navigation task in an audio interference processing system. In accordance with an embodiment, audio navigation instance 50 is configured to present an audio navigation signal 502 to a user 508 in a spatial location within a stereo field 506 according to a panning modulation 602. In accordance with an audio navigation task, the presentation of audio navigation signal 502 during audio navigation instance 50 comprises a prompt to user 508 to provide an input indicative of the spatial location of navigation signal 502 in stereo field 508. By discriminating the spatial location, or pan, of audio navigation signal 502 (e.g. left-right), user 508 can be characterized as "navigating" the stereo field audio navigation instance 50. Audio navigation signal 502 may comprise an audio navigation target comprising one or more note, tone, effect, modulation, or signal characteristic. In certain embodiments, audio navigation signal 502 may comprise an indication of an upcoming audio navigation target, such as a gradual shift in pan, a change in volume, or a note/tone.

Panning modulation 602 is configured to pan the output of audio navigation signal 502 to right transducer 504R and left transducer 504L such that audio navigation signal 502 is presented primarily to right transducer 504R at certain time points in audio navigation instance 50 and is presented primarily to left transducer 504L at certain time points in audio navigation instance 50. Panning modulation 602 is configured to modulate the pan of audio navigation signal 502 to create a spatial effect such that audio navigation signal 502 is heard by the user 508 at different "locations" in stereo field 506. Panning modulation 602 may be configured as an alternating "hard pan," such that the pan of audio navigation signal 502 may alternate between a 0-degree pan, i.e. signal output in only the right transducer 504R, and a 180-degree pan, i.e. signal output in only the left transducer 504L. Alternatively, panning modulation 602 may be dynamically configured to pan at various spatial locations between 0-degrees and 180-degrees pan within the stereo field 506. In embodiments with three or more transducers comprising a surround sound environment, panning modulation 602 may be dynamically configured to pan at various spatial locations between 0-degrees and 360-degrees within the stereo field 506. Panning modulation 602 may be configured according to various difficulty parameters in an audio navigation task. For example, an alternating hard pan between 0-degrees and 180-degrees might define an "easier" audio navigation parameter; whereas a 30-degree pan or a 240-degree pan might define a more "difficult" audio navigation parameter. In certain embodiments, audio navigation signal 502 may be comprised entirely of a panning modulation 602 (i.e., without specific presentation of navigation target tone or sound). In such embodiments, panning modulation 602 may continuously modulate the pan of an audio track across various spatial locations in the stereo field 506, wherein the user 508 is prompted to provide a continuous motion sensor input in response to the spatial placement of the pan in stereo sound field 506.

Figure 6:
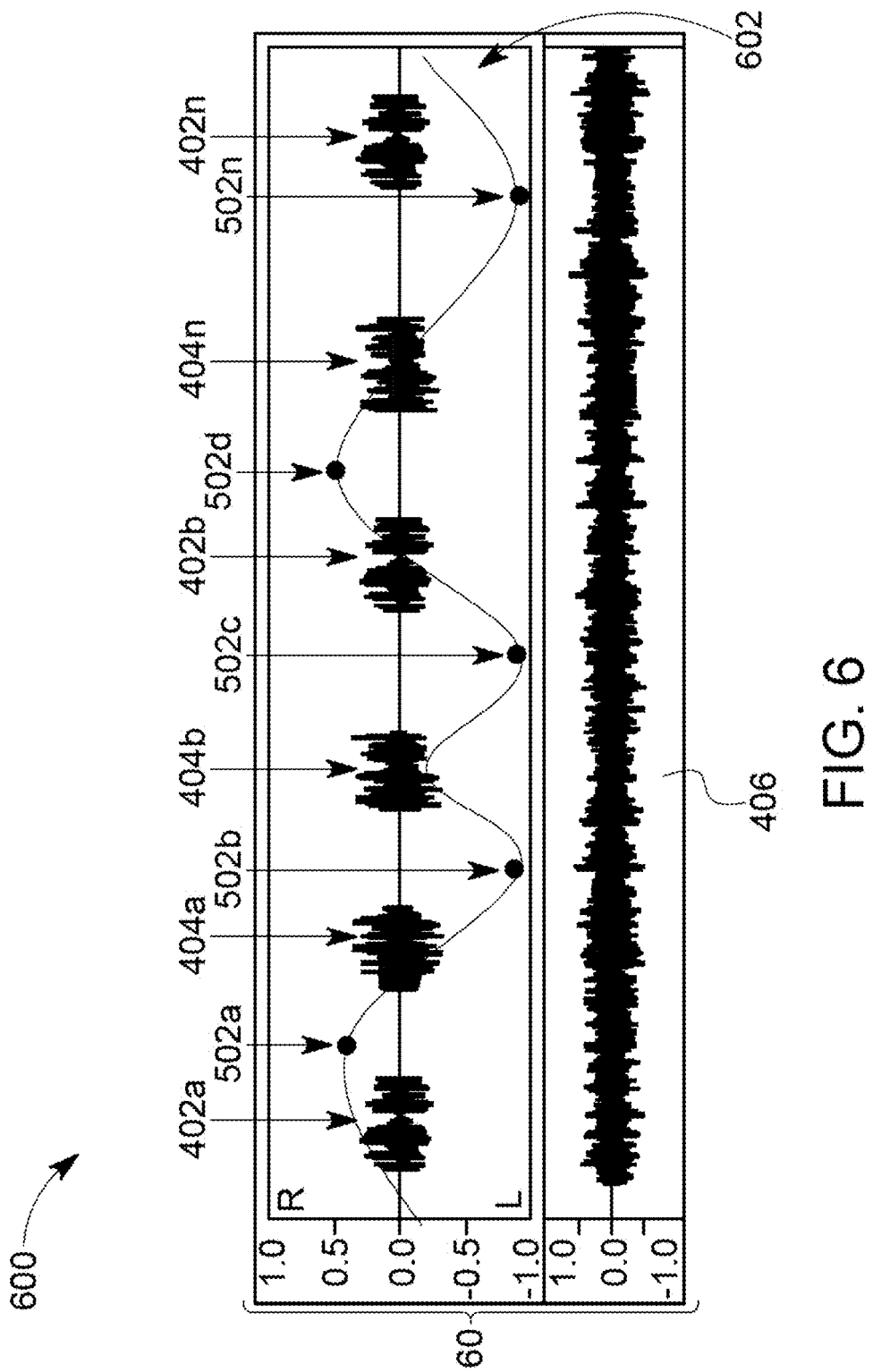
FIG. 6 is a time/amplitude illustration of an audio output comprising an audio interference processing session, in accordance with an embodiment of the present disclosure.

Referring now to FIG. 6, a time/amplitude diagram 600 comprising an audio interference processing instance 60 is shown. In accordance with an embodiment of the present disclosure, an audio interference processing instance 60 comprises an audio output corresponding to simultaneous presentation of an audio target discrimination task and an audio navigation task; for example, the audio target discrimination task described in FIG. 4C and the audio navigation task described in FIG. 5. Audio interference processing instance 60 may comprise periodically presenting one or more audio targets 402a-402n and one or more non-target audio signals 404a-404n at two or more time points, optionally in the presence of background audio file 406 comprising a distractor or interrupter audio signal. Audio interference processing instance 60 may comprise periodically presenting one or more audio navigation signals 502a-502n according to panning modulation 602. In accordance with certain embodiments, the one or more audio targets 402a-402n comprise a series of periodic user prompts for a user to provide a sensor input corresponding to an audio target discrimination task. The one or more non-target audio signals 404a-404n comprise a series of periodic distractions or interruptions associated with the audio target discrimination task. The one or more audio navigation signals 502a-502n comprise a series of periodic user prompts for a user to provide a sensor input corresponding to an audio navigation task. In accordance with certain embodiments, the concurrent presentation of the audio target discrimination task and the audio navigation task is configured to enable an audio multi-tasking environment within an audio-only interference processing system.

Figure 7:
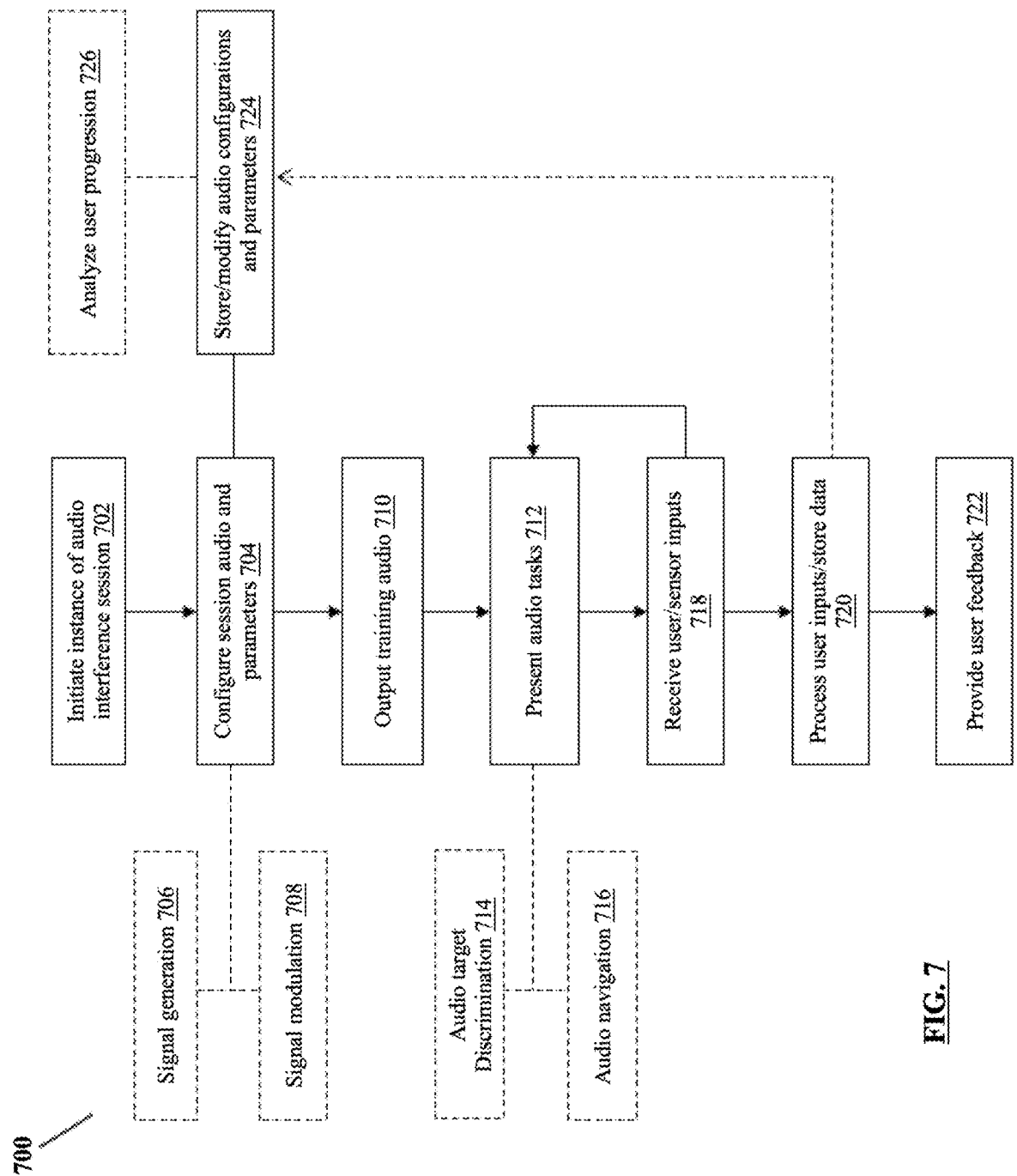
FIG. 7 is a functional block diagram of an audio-only interference processing system and method, in accordance with certain aspects of the present disclosure.

Referring now to FIG. 7, a functional block diagram illustrating a process flow 700 of an audio interference processing system is shown. In accordance with certain aspects of the present disclosure, a user initiates an instance of an audio interference processing session 702. The audio interference processing system configures the audio and control/processing parameters for the session 704. Audio configuration may include executing one or more audio processing functions, such as a signal generation module 706 being operable to generate a target audio sequence and a non-target audio sequence corresponding to an audio target discrimination task, and a signal modulation module 708 being operable to configure a spectral modulation (or other modulation) corresponding to an audio navigation task. Process flow 700 continues by presenting a training audio output 710 to a user to learn/memorize the target audio sequence corresponding to the audio target discrimination task. Process flow 700 continues by presenting an audio output to the user corresponding to one or more audio tasks 712. In accordance with certain embodiments, the one or more audio tasks 712 may comprise an audio target discrimination task 714 (such as the audio target discrimination task described in FIGS. 4B and 4C, above) and an audio navigation task 716 (such as the audio navigation task described in FIG. 5, above). Audio target discrimination task 714 and audio navigation task 716 may be presented independently or concurrently within one or more instances of the audio interference processing session 702. Process flow 700 continues by receiving sensor inputs from the user in the interference processing session 718, wherein the user inputs correspond to audio task prompts corresponding with the audio target discrimination task 714 and/or audio navigation task 716. The system may continuously receive sensor inputs from the user throughout the instance of the interference processing session 702. Process flow 700 continues by processing the inputs according to one or more input parameters and storing the input data in memory 720. In accordance with certain embodiments, the one or more input parameters may comprise task parameters (e.g. a specific action associated with a specific audio prompt), input parameters (e.g. a specific type of input associated with a specific audio prompt), and/or timing parameters (e.g. a specific action time frame in which a user is required to provide an input in response to a specific audio prompt). Process flow 700 may continue by providing a feedback output to the user in response to processing the user inputs 722. The feedback output may be indicative with a user's performance according to the one or more input parameters. The feedback output may comprise an audio output, as well as one or more alternative output modalities. Process flow 700 may continue by storing the user input data from the audio interference processing session and optionally analyzing that data to modify one or more audio configurations and/or control/processing parameters for subsequent instances of an audio interference processing session 724. Process flow 700 may optionally continue by analyzing the user input data from the present instance of an audio interference processing session against historical user input data from one or more past instances to analyze user progress in an audio interference processing regimen 726. The analysis of user progression may comprise one or more quantitative measures of an improvement to a user's cognitive skill or ability over a defined period of time.

Figure 8:
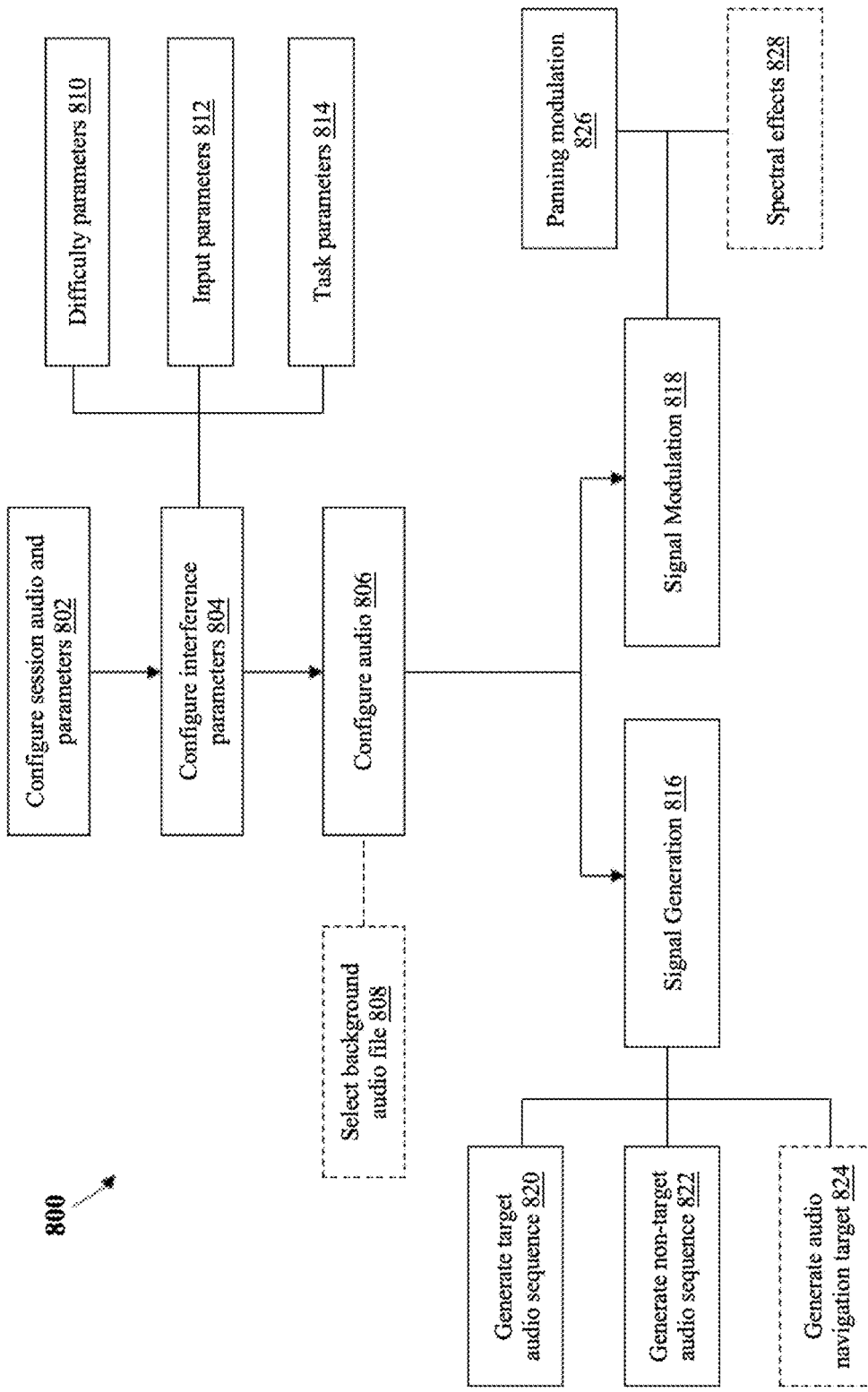
FIG. 8 is a functional block diagram of a routine of an audio-only interference processing system and method, in accordance with certain aspects of the present disclosure.

Referring now to FIG. 8, a functional block diagram of a routine 800 of an audio-only interference processing system and method is shown. In accordance with certain aspects of the present disclosure, routine 800 provides for various aspects of configuring one or more audio processing controls, application controls and parameters, and data processing parameters. Routine 800 may begin with configuring audio controls and parameters and interference processing parameters for an instance of an audio interference processing session 802. Routine 800 continues by configuring interference parameters 804 for the interference processing session 804. In accordance with certain embodiments, interference parameters comprise difficulty parameters 810 (e.g. audio sequence complexity and/or audio navigation complexity); input parameters 812 (e.g. the type of sensor input corresponding to the task prompt, the timing of the sensor input, and other specific sensor input characteristics); and task parameters 814 (e.g. task type, such as navigation and discrimination; task presentation, such as order of tasks; and other task parameters). Routine 800 continues by configuring one or more audio outputs 806 associated with the instance of the audio interference processing session. In certain embodiments, audio task prompts are presented in the presence of a background audio file 808, wherein the background audio file comprises a distraction or interruption within the audio interference processing session. Audio configuration 806 may further comprise one or more signal generation functions 816 and/or one or more signal modulation functions 818. Signal generation functions 816 may comprise one or more audio processing modules operably configured to systematically or randomly generate a target audio sequence 820; one or more audio processing modules operably configured to systematically or randomly generate a non-target audio sequence 822; and, optionally, one or more audio processing modules operably configured to systematically or randomly generate navigation audio target 824. Signal modulation functions 818 may comprise one or more audio processing modules operably configured to systematically or randomly configure a panning modulation 826; and/or one or more audio processing modules operably configured to systematically or randomly configure one or more spectral effects 828.

Figure 9:
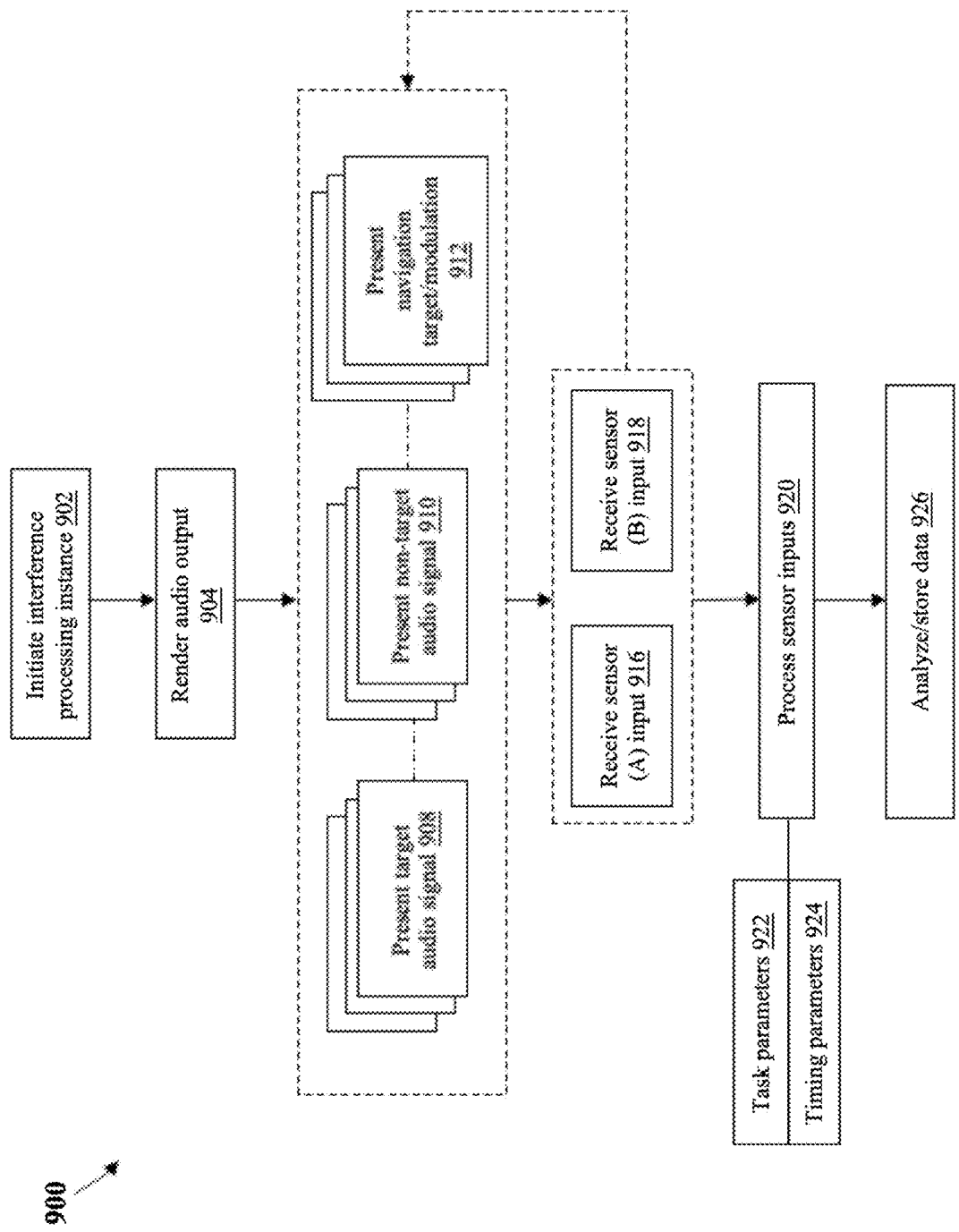
FIG. 9 is a functional block diagram of a routine of an audio-only interference processing system and method, in accordance with certain aspects of the present disclosure.

Referring now to FIG. 9, a functional block diagram of a routine 900 of an audio-only interference processing system and method is shown. In accordance with certain aspects of the present disclosure, routine 900 provides for various aspects of executing an instance of an audio interference processing session. Routine 900 may begin with initiating an audio interference processing session 902. Routine 900 may continue by rendering an audio output to one or more acoustic transducers, wherein the audio output comprises one or more audio prompts corresponding to one or more audio-based tasks 904. In accordance with certain embodiments, the audio output may comprise periodically presenting, at one or more points in a specified time period, a target audio signal 908, a non-target audio signal 910, and an audio navigation target/navigation modulation 912. Routine 900 continues by continuously receiving, for the duration of the instance of the audio interference processing session, at least one of a sensor input 916 and a sensor input 918, wherein sensor input 916 corresponds to a first sensor type (e.g., a touch sensor) and sensor input 918 corresponds to a second sensor type (e.g., a motion sensor). Routine 900 may continue by processing the sensor inputs 920 corresponding to one or more user inputs in response to one or more audio task prompts within the audio interference processing session, according to one or more processing parameters. In accordance with certain embodiments, one or more processing parameters may comprise task parameters 922 (e.g. associating a specific input type with a specific task prompt) and timing parameters (e.g. one or more time-window in which the sensor input may be received in response to the specific task prompt). Routine 900 may continue by analyzing the processed user-input data to derive one or more performance metrics associated with the user's performance of the audio interference processing tasks, and may store the data/analysis in an application database 926 for future retrieval and further processing.

Figure 10:
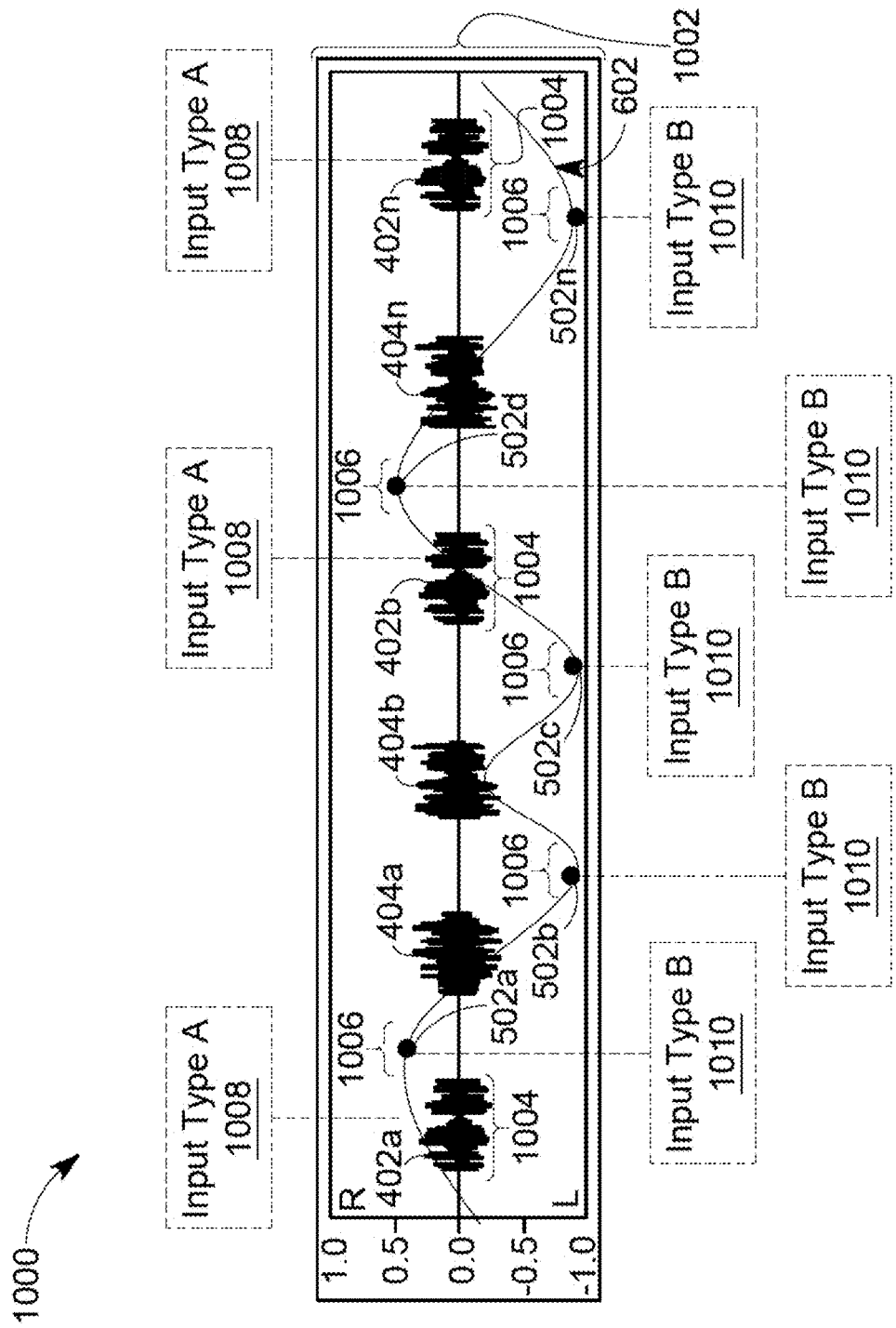
FIG. 10 is a time/amplitude illustration depicting a temporal relationship between sensor inputs and audio outputs in an instance of an audio interference processing session, in accordance with one or more aspects of the present disclosure.

Referring now to FIG. 10, a time/amplitude diagram 1000 illustrating temporal relationships between sensor inputs and audio outputs in an instance of an audio interference processing instance 1002 is shown. In in accordance with one or more aspects of the present disclosure, an audio interference processing instance 1002 comprises an audio output corresponding to simultaneous presentation of an audio target discrimination task and an audio navigation task; for example, the audio target discrimination task described in FIG. 4C and the audio navigation task described in FIG. 5. Audio interference processing instance 1002 may comprise periodically presenting one or more audio targets 402a-402n and one or more non-target audio signals 404a-404n at two or more time points during audio interference processing instance 1002. Audio interference processing instance 1002 may comprise periodically presenting one or more audio navigation signals 502a-502n according to panning modulation 602. In accordance with certain embodiments, the one or more audio targets 402a-402n comprise a series of periodic user prompts for a user to provide a sensor input 1008 corresponding to an audio target discrimination task. In accordance with certain embodiments, sensor input 1010 corresponds to a first sensor type (e.g., a touch sensor). In accordance with certain embodiments, audio interference processing instance 1002 may comprise a first sensor input time window 1004 in which the user may provide sensor input 1008. The one or more non-target audio signals 404a-404n comprise a series of periodic distractions or interruptions associated with the audio target discrimination task. The one or more audio navigation signals 502a-502n comprise a series of periodic user prompts for a user to provide a sensor input 1010 corresponding to an audio navigation task. In accordance with certain embodiments, sensor input 1008 corresponds to a second sensor type (e.g. a motion sensor). In accordance with certain embodiments, audio interference processing instance 1002 may comprise a second sensor input time window 1006 in which the user may provide sensor input 1010. In accordance with certain embodiments, the concurrent presentation of the audio target discrimination task and the audio navigation task is configured to enable an audio multi-tasking environment within an audio-only interference processing system.

Figure 11:
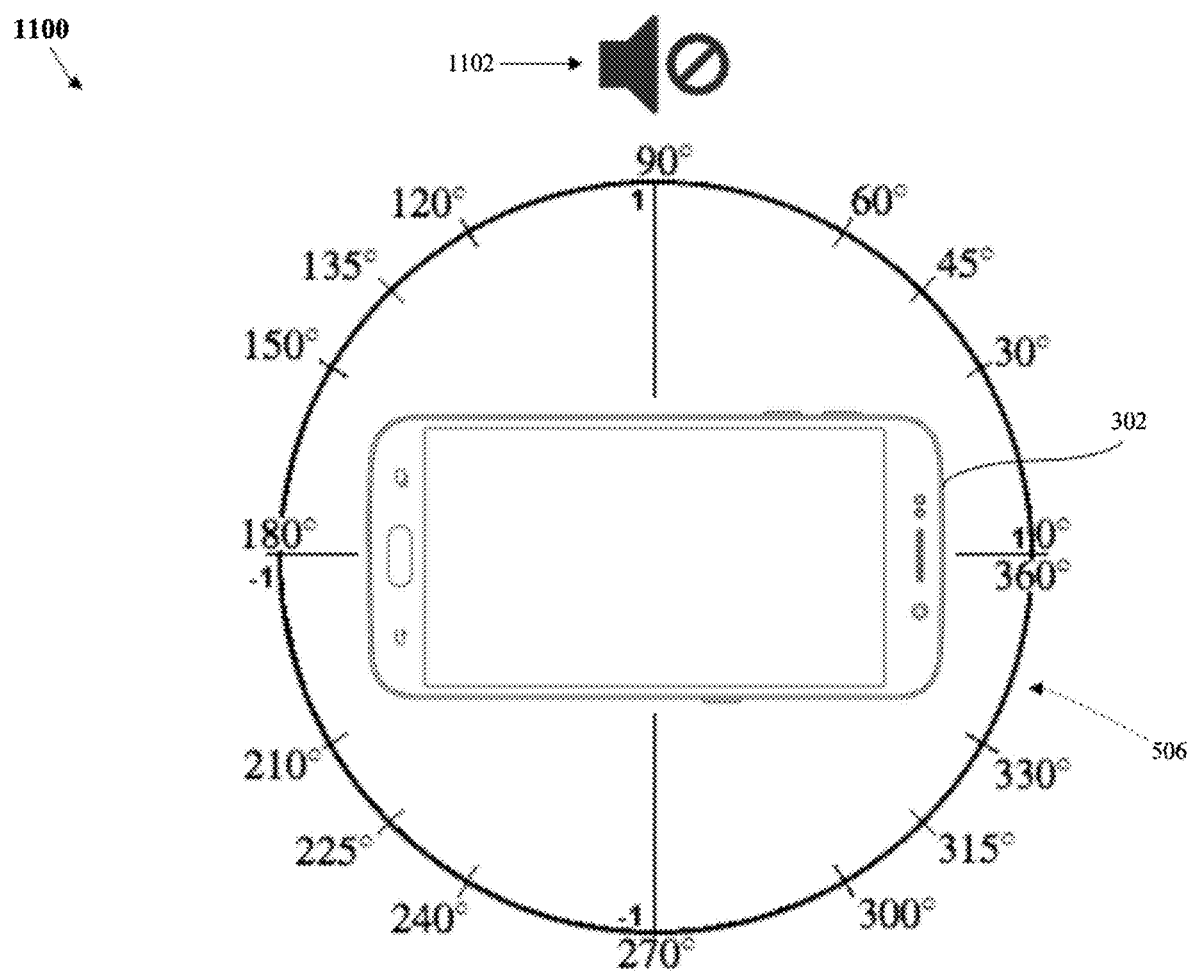
FIGS. 11-21 are functional illustrations of various user inputs in response to audio outputs comprising one or more instances of an audio-only interference processing session, in accordance with certain illustrative embodiments of the present disclosure.
Figure 12:
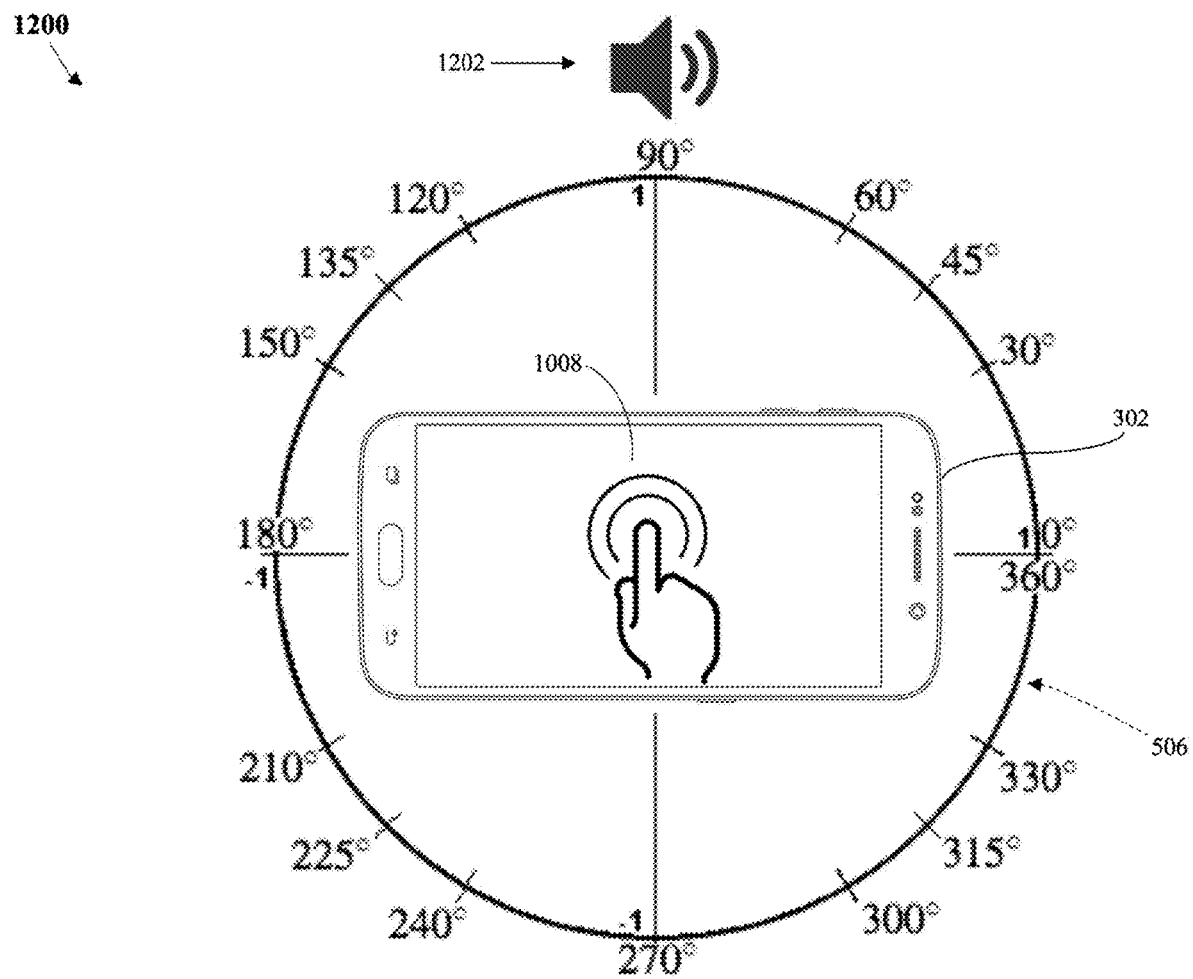
Figure 13:
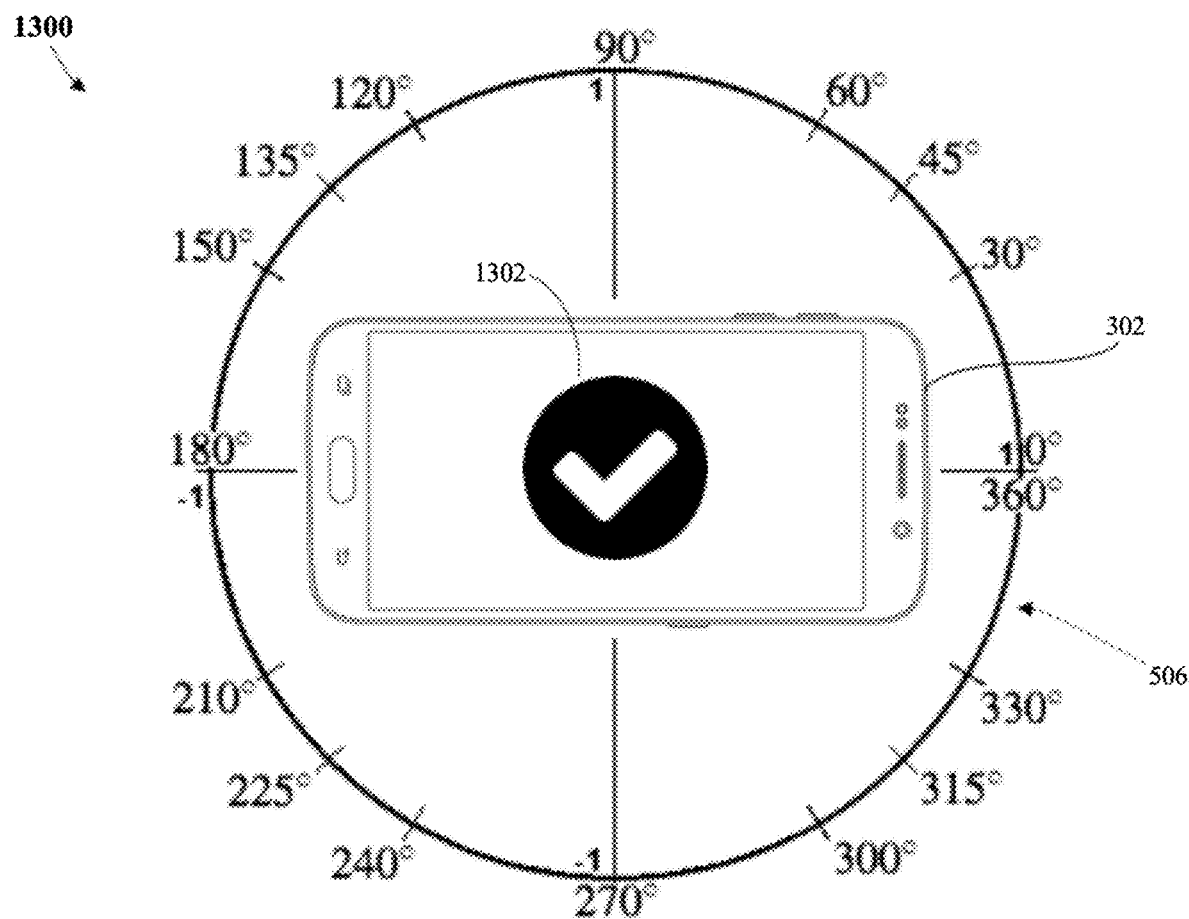
Figure 14:
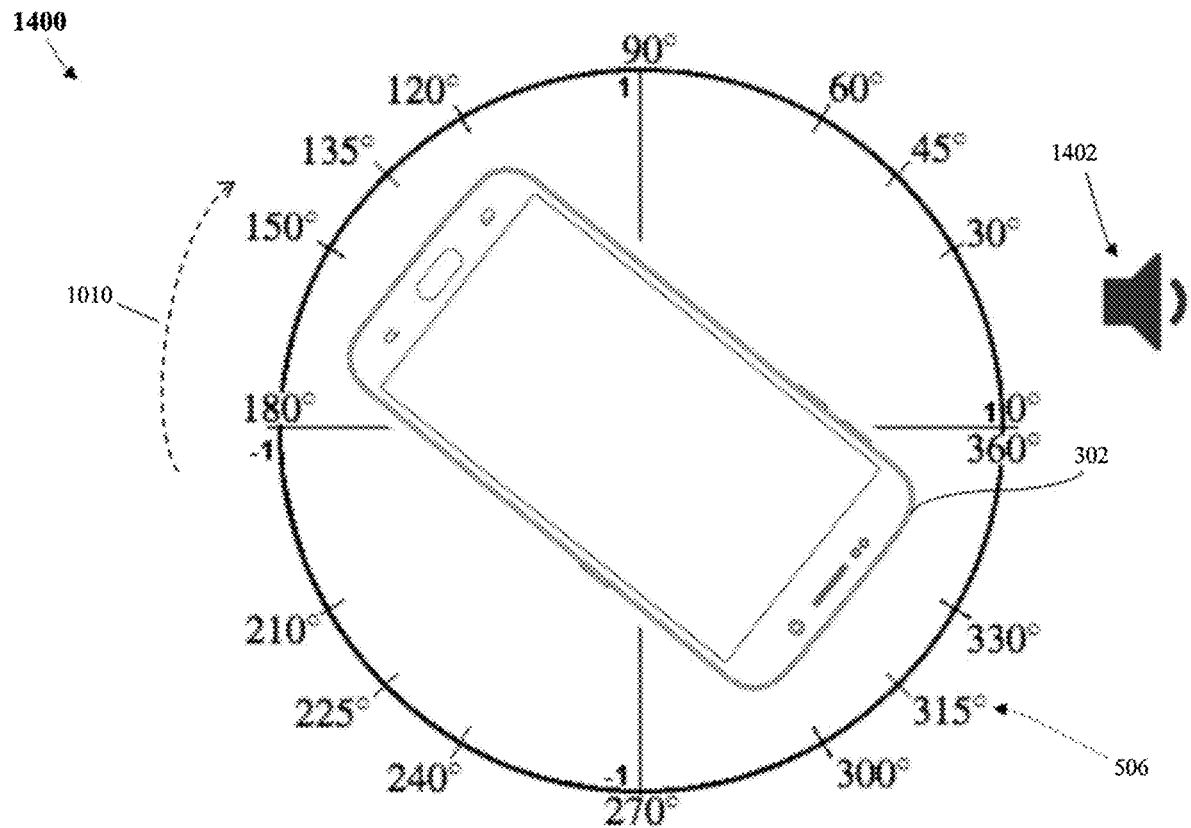
Figure 15:
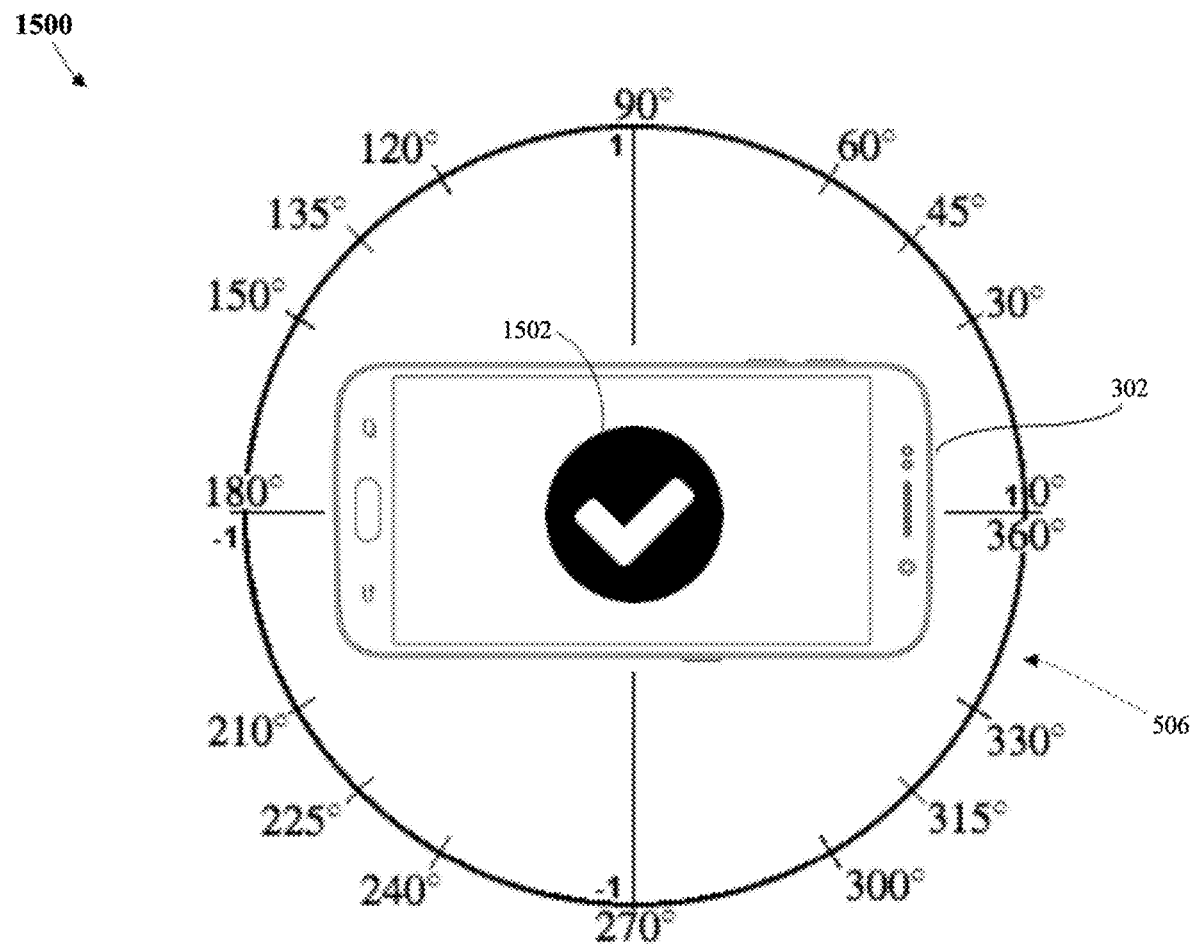
Figure 16:
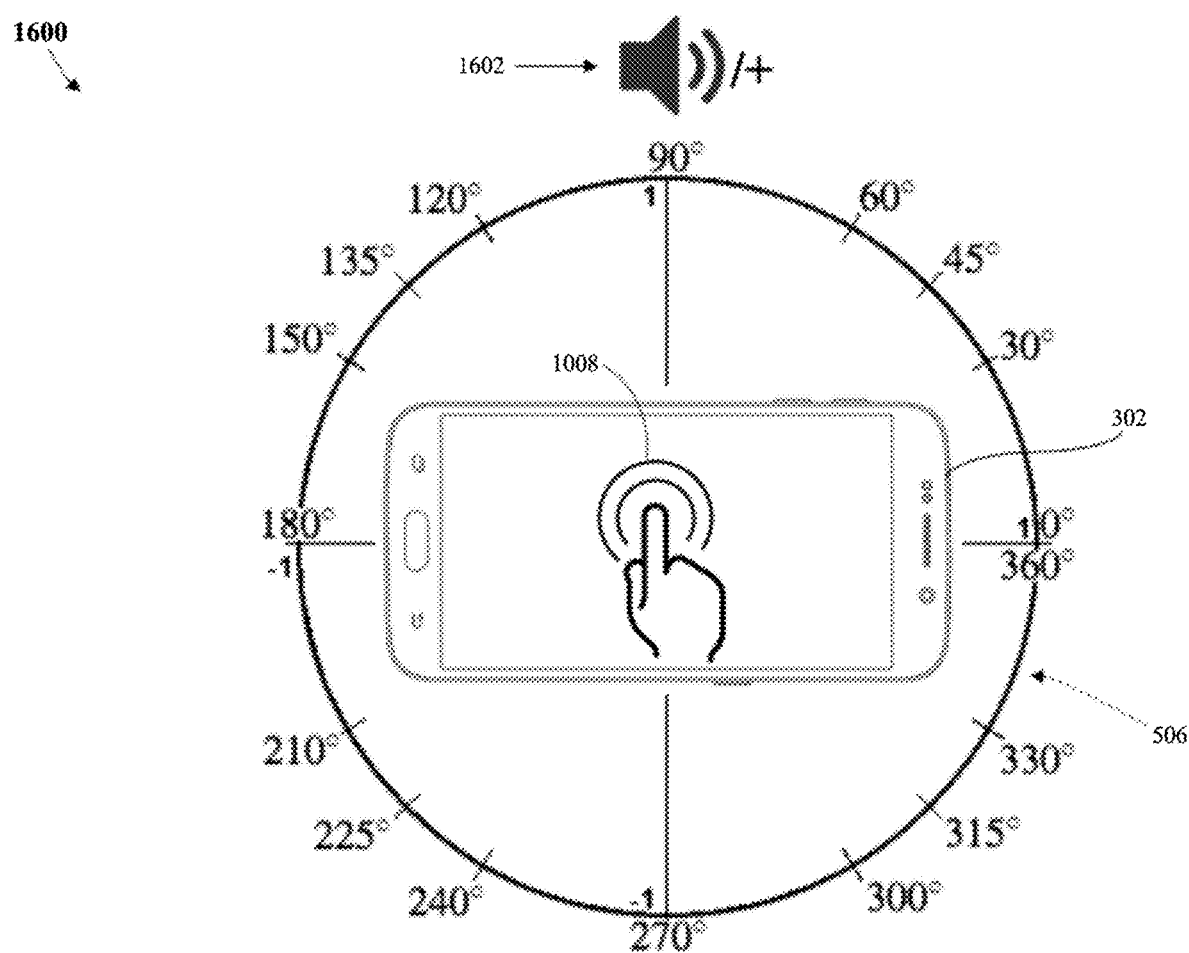
Figure 17:
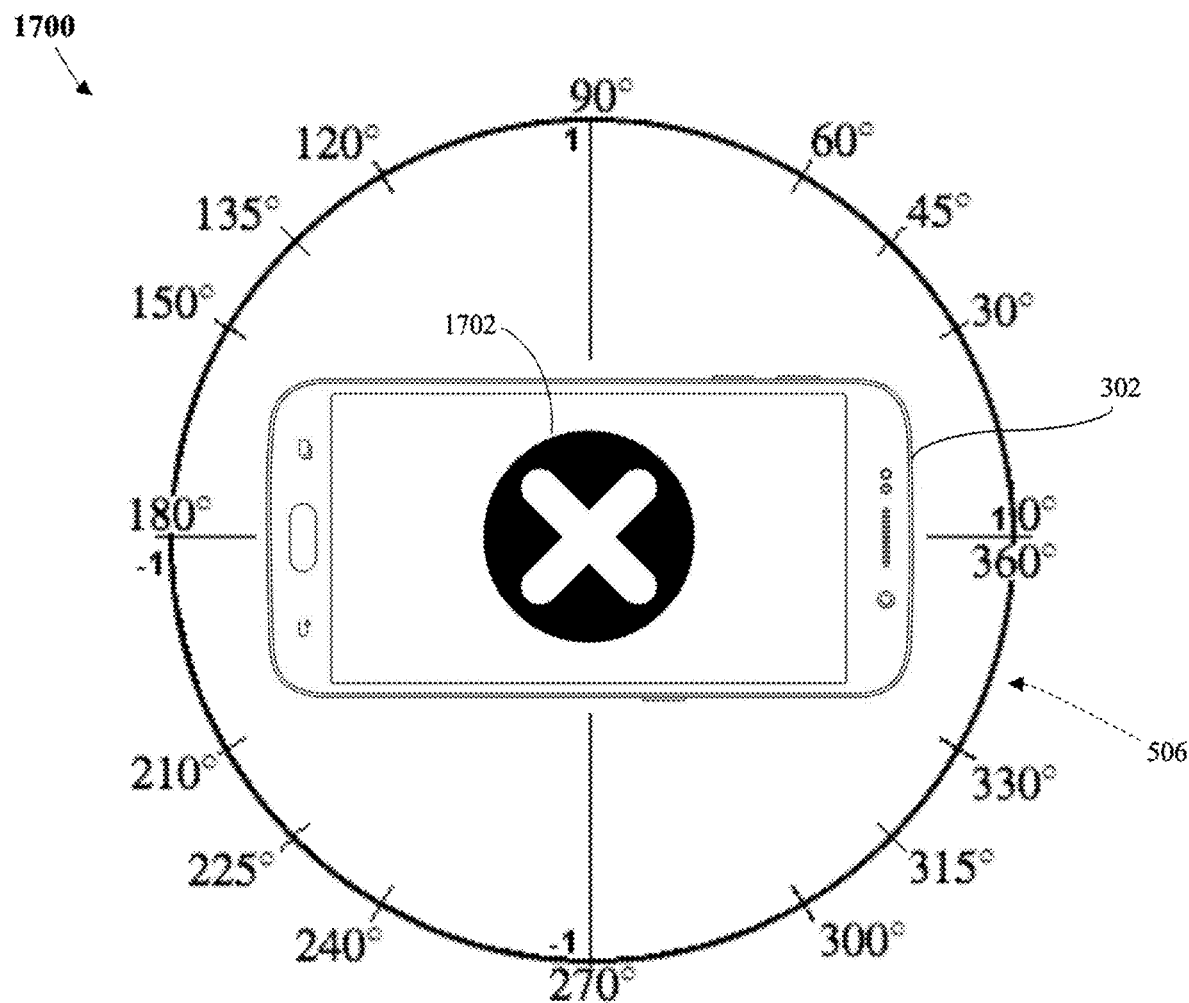
Figure 18:
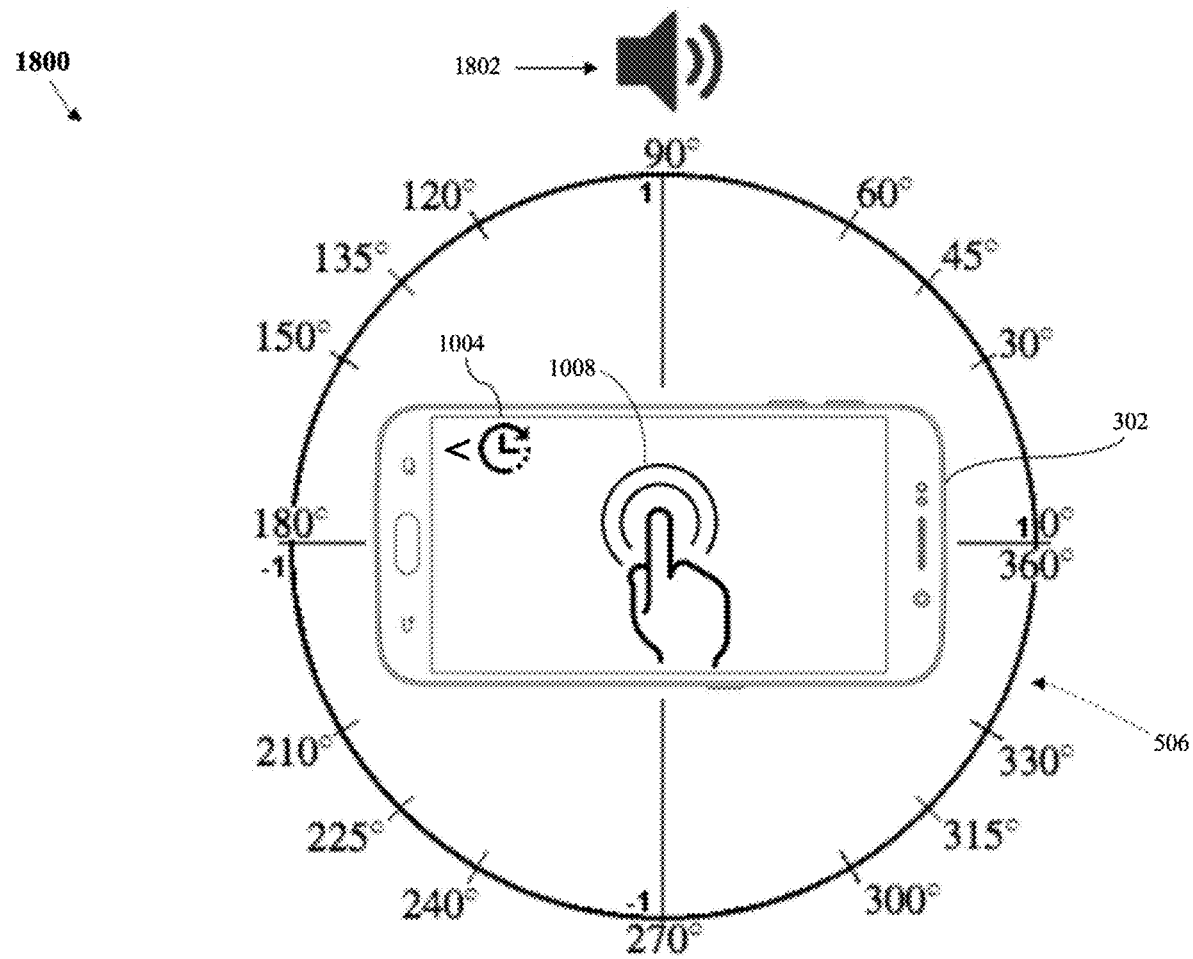
Figure 19:
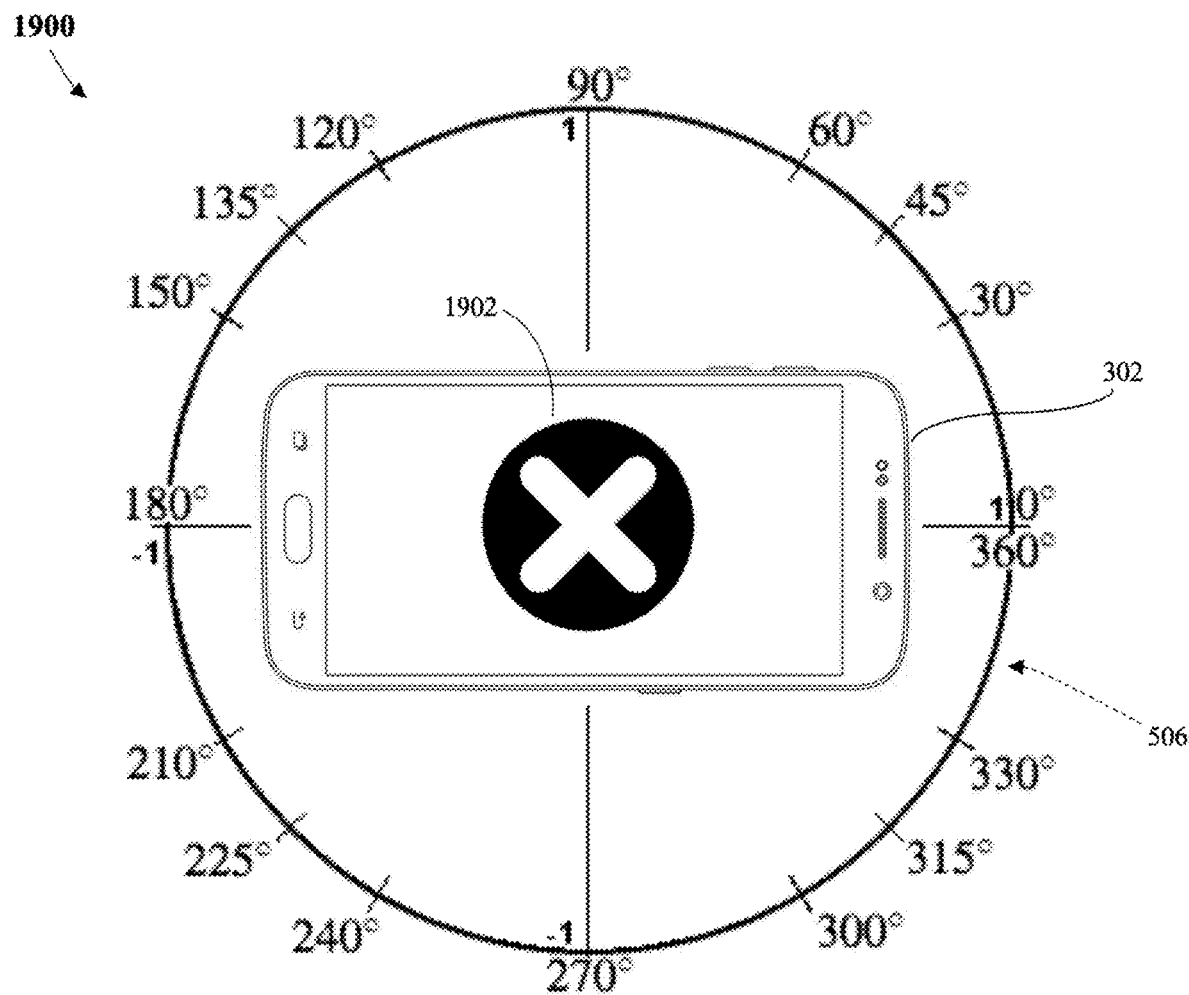
Figure 20:
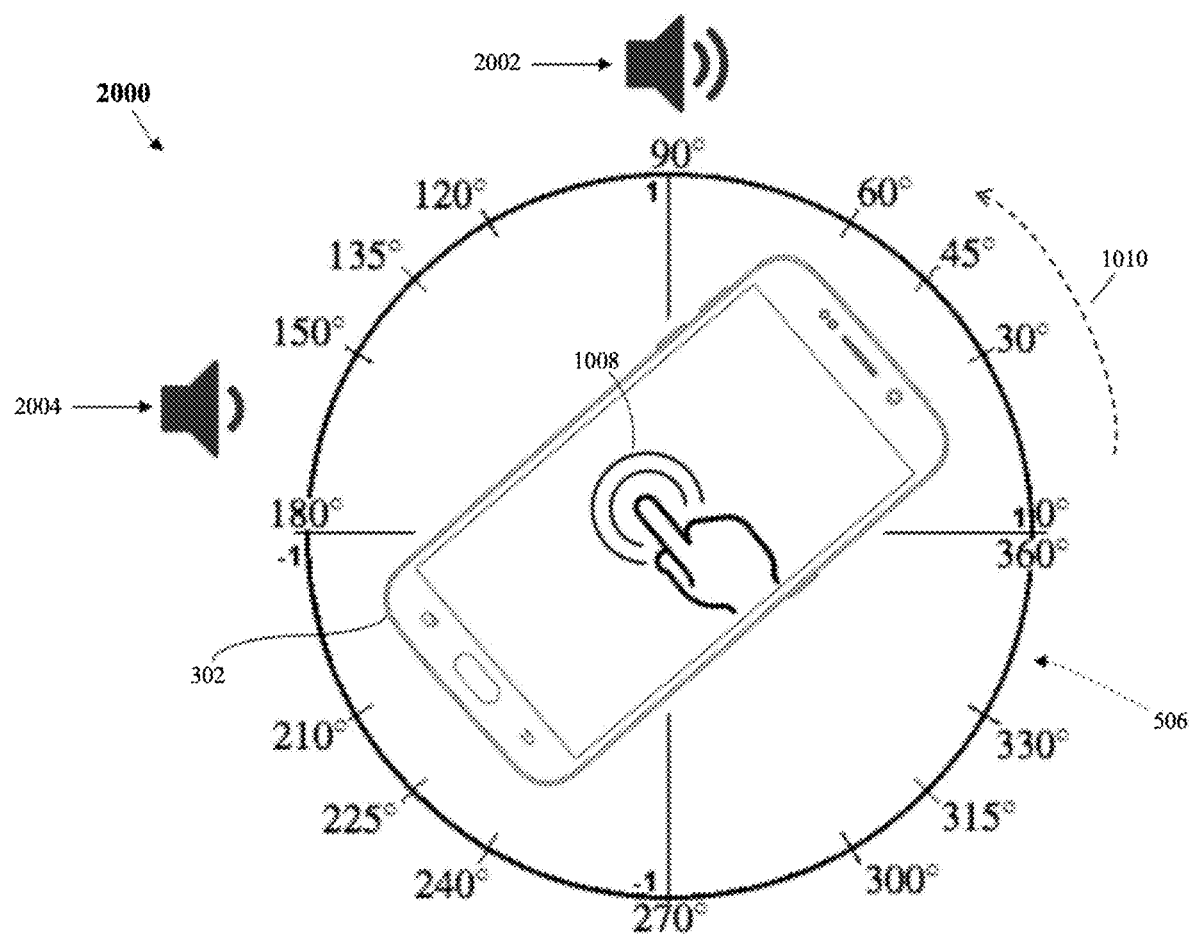
Figure 21:
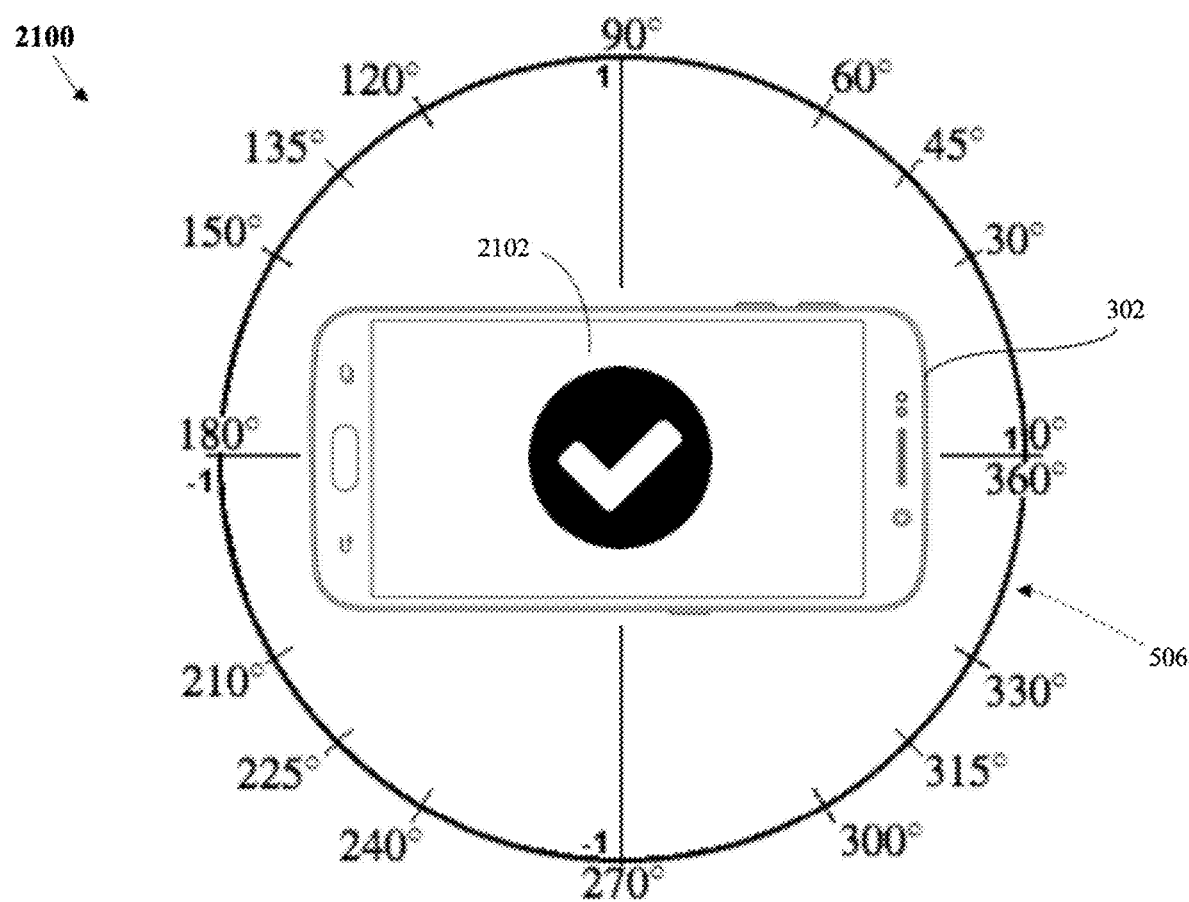

Referring now to FIGS. 11-21, a plurality of functional diagrams illustrative of a plurality of user interactions comprising one or more instances of an audio-only interference processing session is shown. In accordance with one or more illustrative embodiments of the present disclosure, FIG. 11 shows a user interaction 1100 within an audio interference processing session comprises a mobile electronic device 302 being oriented in a stereo field 506, wherein the user is presented with a training audio output 1102. The user does not provide an input in response to training audio output 1102. In FIG. 12, a user interaction 1200 comprises an output of an audio target 1202 in response to which a user provides a touch input 1008 via mobile electronic device 302. A user interaction 1300 in FIG. 13 comprises a feedback output 1302 to the user indicating the user provided the correct input in response to the audio target 1202 (in FIG. 12) within the specified input window. The feedback output may be embodied as a visual output on mobile electronic device 302 and/or an audio output or haptic output. A user interaction 1400 shown in FIG. 14 comprises an output of an audio navigation target 1402, in response to which a user provides a motion input 1010 by turning mobile electronic device 302 toward the location of audio navigation target 1402 within stereo field 506. In FIG. 15, a user interaction 1500 comprises a feedback output 1502 to the user indicating the user provided the correct input in response to the audio navigation target 1402 (FIG. 14) within a specified time window. A user interaction 1600 in FIG. 16 comprises an output of a non-target audio signal 1602, in response to which the user provides a touch input 1008 via mobile electronic device 302. A user interaction 1700 in FIG. 17 comprises a feedback output 1702 to the user indicating the user provided an incorrect input in response to the non-target audio signal 1602. In FIG. 18, a user interaction 1800 comprises an output of an audio target 1802, in response to which the user provides a touch input 1008 via mobile electronic device 302 outside of the specified time window. A user interaction 1900 in FIG. 19 comprises a feedback output 1902 to the user indicating the user input was outside of the specified time window or otherwise did not comply with an input parameter. A user interaction 2000 in FIG. 20 comprises an output of an audio target 2002 and an audio navigation target 2004 (either simultaneously or in close succession) in response to which the user provides a touch input 1008 via mobile electronic device 302 and a motion input 1010 (either simultaneously or in close succession) by turning mobile electronic device 302 toward the location of audio navigation target 2004 within stereo field 506. A user interaction 2100 in FIG. 21 comprises a feedback output 2102 to the user indicating the user provided the correct input in response to the audio target 2002 (FIG. 20) and the audio navigation target 2004 within the specified input window.

Figure 22:
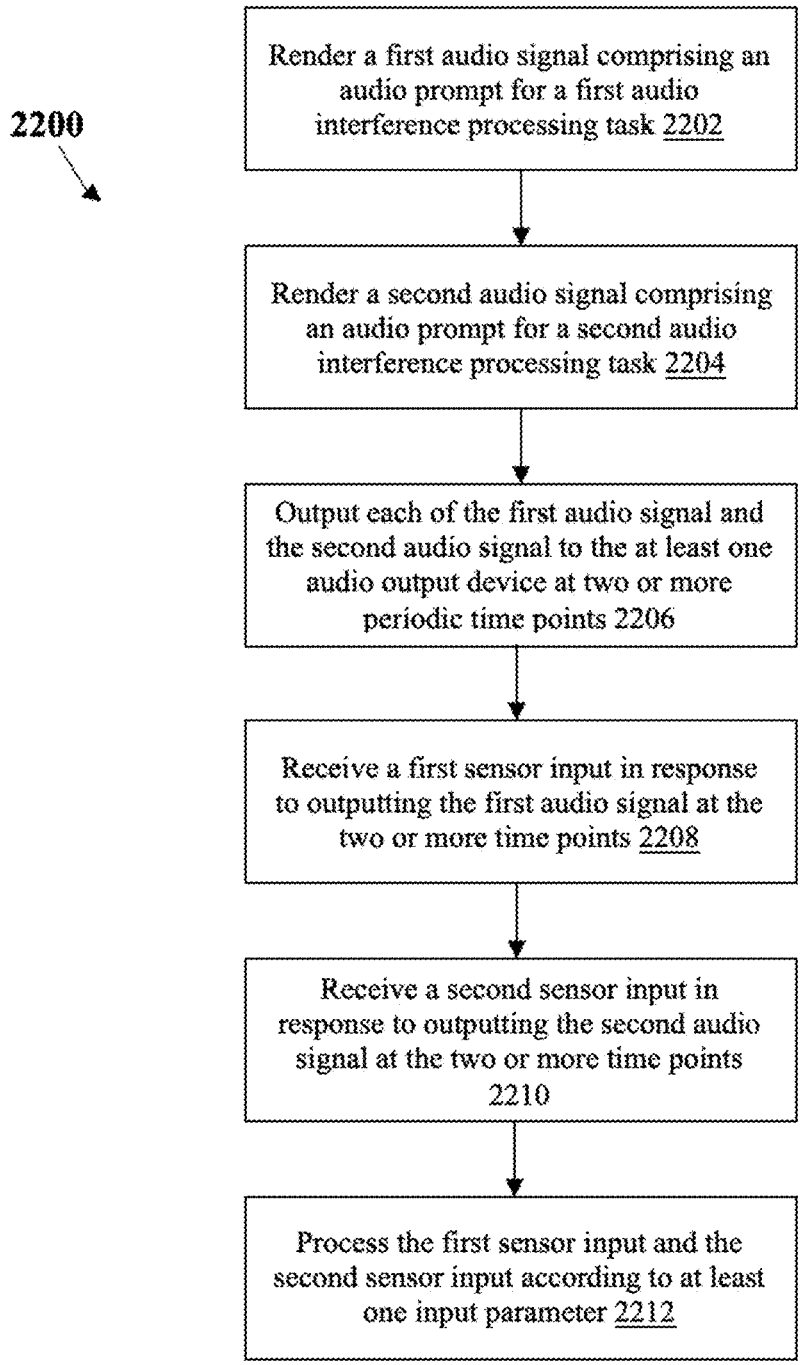
FIG. 22 is a method flow chart of an audio-only interference processing method, in accordance with an aspect of the present disclosure.

Referring now to FIG. 22, a method flow chart of an audio interference processing method 2200 is shown. In accordance with an aspect of the present disclosure, audio-only interference processing method 2200 comprises rendering, with a processing unit, a first audio signal comprising an audio prompt for a first audio interference processing task 2202, the first audio signal comprising a first signal sequence or first modulation parameter. Method 2200 continues by rendering, with the processing unit, a second audio signal comprising an audio prompt for a second audio interference processing task 2204, the second audio signal comprising a second signal sequence or second modulation parameter. Method 2200 continues by outputting, with an audio output device, each of the first audio signal and the second audio signal to the at least one audio output device at two or more periodic time points 2206, wherein the two or more periodic time points comprise an instance of an audio interference processing session. Method 2200 continues by receiving, with the processing unit, a first sensor input in response to outputting the first audio signal at the two or more time points 2208. Method 2200 continues by receiving, with the processing unit, a second sensor input in response to outputting the second audio signal at the two or more time points 2210. Method 2200 continues by processing, with the processor, the first sensor input and the second sensor input according to at least one input parameter 2212, the at least one input parameter comprising a timing parameter and a task parameter. In accordance with certain embodiments of method 2200, the first sensor input may comprise an audio target discrimination input, wherein the first audio interference processing task is an audio target discrimination task; and, the second sensor input may comprise an audio navigation input, wherein the second audio interference processing task is an audio navigation task.

Method 2200 may further comprise rendering, with the processing unit, a third audio signal comprising an audio interference output in the instance of the audio interference processing session. In accordance with certain embodiments, method 2200 may further comprise modifying, with the processor, the at least one input parameter in response to processing the first sensor input and the second sensor input, according to at least one task performance parameter.

Certain embodiments of method 2200 may further comprise modifying, with the processor, the first signal sequence or first modulation parameter of the first audio signal in response to processing the first or second sensor input, according to at least one task performance parameter. Method 2200 may further comprise modifying, with the processor, the second signal sequence or second modulation parameter of the second audio signal in response to processing the first or second sensor input, according to at least one task performance parameter. In accordance with certain embodiments of method 2200, the first audio signal may comprise a randomly generated audio sequence comprising a subject audio target.

In accordance with certain embodiments of method 2200, the second sensor input may comprise turning a mobile electronic device in a direction of the second audio signal in a stereo field. The first audio signal comprises a randomly generated audio sequence comprising a subject audio target, and the second audio signal comprises a panning modulation comprising a directional audio prompt.

As will be appreciated by one of skill in the art, the present invention may be embodied as a method (including, for example, a computer-implemented process, a business process, and/or any other process), apparatus (including, for example, a system, machine, device, computer program product, and/or the like), or a combination of the foregoing. Accordingly, embodiments of the present invention may take the form of an entirely hardware embodiment, an entirely software embodiment (including firmware, resident software, micro-code, etc.), or an embodiment combining software and hardware aspects that may generally be referred to herein as a "system." Furthermore, embodiments of the present invention may take the form of a computer program product on a computer-readable medium having computer-executable program code embodied in the medium.

Any suitable transitory or non-transitory computer readable medium may be utilized. The computer readable medium may be, for example but not limited to, an electronic, magnetic, optical, electromagnetic, infrared, or semiconductor system, apparatus, or device. More specific examples of the computer readable medium include, but are not limited to, the following: an electrical connection having one or more wires; a tangible storage medium such as a portable computer diskette, a hard disk, a random access memory (RAM), a read-only memory (ROM), an erasable programmable read-only memory (EPROM or Flash memory), a compact disc read-only memory (CD-ROM), or other optical or magnetic storage device.

In the context of this document, a computer readable medium may be any medium that can contain, store, communicate, or transport the program for use by or in connection with the instruction execution system, apparatus, or device. The computer usable program code may be transmitted using any appropriate medium, including but not limited to the Internet, wireline, optical fiber cable, radio frequency (RF) signals, or other mediums.

Computer-executable program code for carrying out operations of embodiments of the present invention may be written in an object oriented, scripted or unscripted programming language such as Java, Perl, Smalltalk, C++, or the like. However, the computer program code for carrying out operations of embodiments of the present invention may also be written in conventional procedural programming languages, such as the "C" programming language or similar programming languages.

Embodiments of the present invention are described above with reference to flowchart illustrations and/or block diagrams of methods, apparatus (systems), and computer program products. It will be understood that each block of the flowchart illustrations and/or block diagrams, and/or combinations of blocks in the flowchart illustrations and/or block diagrams, can be implemented by computer-executable program code portions. These computer-executable program code portions may be provided to a processor of a general purpose computer, special purpose computer, or other programmable data processing apparatus to produce a particular machine, such that the code portions, which execute via the processor of the computer or other programmable data processing apparatus, create mechanisms for implementing the functions/acts specified in the flowchart and/or block diagram block or blocks.

These computer-executable program code portions may also be stored in a computer-readable memory that can direct a computer or other programmable data processing apparatus to function in a particular manner, such that the code portions stored in the computer readable memory produce an article of manufacture including instruction mechanisms which implement the function/act specified in the flowchart and/or block diagram block(s).

The computer-executable program code may also be loaded onto a computer or other programmable data processing apparatus to cause a series of operational phases to be performed on the computer or other programmable apparatus to produce a computer-implemented process such that the code portions which execute on the computer or other programmable apparatus provide phases for implementing the functions/acts specified in the flowchart and/or block diagram block(s). Alternatively, computer program implemented phases or acts may be combined with operator or human implemented phases or acts in order to carry out an embodiment of the invention.

As the phrase is used herein, a processor may be "configured to" perform a certain function in a variety of ways, including, for example, by having one or more general-purpose circuits perform the function by executing particular computer-executable program code embodied in computer-readable medium, and/or by having one or more application-specific circuits perform the function.

Embodiments of the present invention are described above with reference to flowcharts and/or block diagrams. It will be understood that phases of the processes described herein may be performed in orders different than those illustrated in the flowcharts. In other words, the processes represented by the blocks of a flowchart may, in some embodiments, be performed in an order other that the order illustrated, may be combined or divided, or may be performed simultaneously. It will also be understood that the blocks of the block diagrams illustrated, in some embodiments, merely conceptual delineations between systems and one or more of the systems illustrated by a block in the block diagrams may be combined or share hardware and/or software with another one or more of the systems illustrated by a block in the block diagrams. Likewise, a device, system, apparatus, and/or the like may be made up of one or more devices, systems, apparatuses, and/or the like. For example, where a processor is illustrated or described herein, the processor may be made up of a plurality of microprocessors or other processing devices which may or may not be coupled to one another. Likewise, where a memory is illustrated or described herein, the memory may be made up of a plurality of memory devices which may or may not be coupled to one another.

While certain exemplary embodiments have been described and shown in the accompanying drawings, it is to be understood that such embodiments are merely illustrative of, and in no way are intended to restrict, the broad scope of the invention, and that this invention not be limited to the specific constructions and arrangements shown and described, since various other changes, combinations, omissions, modifications and substitutions, in addition to those set forth in the above paragraphs, are possible. Those skilled in the art will appreciate that various adaptations and modifications of the just described embodiments can be configured without departing from the scope and spirit of the invention. Therefore, it is to be understood that, within the scope of the appended claims, the invention may be practiced other than as specifically described herein.

What is claimed is:

1. A computer-implemented method for audio-based cognitive training, comprising:
presenting, with a processing unit, a first audio signal comprising a first audio prompt, the first audio signal comprising a first signal sequence or a first modulation parameter;

presenting, with the processing unit, a second audio signal comprising a second audio prompt, the second audio signal comprising a second signal sequence or a second modulation parameter;

outputting, with an audio output device, each of the first audio signal and the second audio signal to at least one audio output device at two or more periodic time points;

receiving, with the processing unit, a first sensor input in response to outputting the first audio signal at the two or more time points;

receiving, with the processing unit, a second sensor input in response to outputting the second audio signal at the two or more time points; and processing, with the processor, the first sensor input and the second sensor input according to at least one input parameter, wherein the first sensor input or the second sensor input comprises a motion sensor input in response to a listener turning an input device in a direction of the first audio signal or the second audio signal in a stereo field.

2. The method of claim 1 wherein the first sensor input comprises an audio target discrimination input associated with an audio target discrimination task.

3. The method of claim 1 wherein the second sensor input comprises an audio navigation input associated with an audio navigation task.

4. The method of claim 1 further comprising presenting, with the processing unit, a third audio signal comprising an audio interference output.

5. The method of claim 1 further comprising modifying, with the processing unit, the at least one input parameter in response to processing the first sensor input and the second sensor input, according to at least one performance parameter.

6. The method of claim 1 further comprising modifying, with the processing unit, the first signal sequence or first modulation parameter of the first audio signal in response to processing the first or second sensor input, according to at least one performance parameter.

7. The method of claim 6 further comprising modifying, with the processing unit, the second signal sequence or second modulation parameter of the second audio signal in response to processing the first or second sensor input, according to the at least one performance parameter.

8. The method of claim 1 wherein the first audio signal comprises a randomly generated audio sequence comprising a subject audio target.

9. The method of claim 1 wherein the at least one input parameter comprising a timing parameter and a task parameter.

10. An audio-based system for improving cognition in an individual, the system comprising:

at least one audio output device comprising at least one speaker or headphones;

a mobile electronic device comprising at least one sensor and being operably configured to provide an audio signal to the at least one audio output device, the at least one sensor comprising at least one of a touch sensor and a motion sensor;

an integral or remote processor communicatively engaged with the mobile electronic device; and a non-transitory computer readable medium having instructions stored thereon that, when executed, cause the processor to perform one or more operations, the one or more operations comprising:

rendering a first audio signal comprising a first audio prompt, the first audio signal comprising a first signal sequence or first modulation parameter;

rendering a second audio signal comprising a second audio prompt, the second audio signal comprising a second signal sequence or second modulation parameter;

outputting each of the first audio signal and the second audio signal to the at least one audio output device at two or more periodic time points;

receiving a first sensor input in response to outputting the first audio signal at the two or more time points;

receiving a second sensor input in response to outputting the second audio signal at the two or more time points; and processing the first sensor input and the second sensor input according to at least one input parameter, wherein the first sensor input or the second sensor input comprises a motion sensor input in response to the individual turning the mobile electronic device in a direction of the first audio signal or the second audio signal in a stereo field.

11. The system of claim 10 wherein the one or more operations further comprise generating the first audio signal and the second audio signal according to one or more audio processing modules comprising at least one of a random sequence generator and a modulator.

12. The system of claim 10 wherein the one or more operations further comprise rendering a third audio signal comprising an audio interference output.

13. The system of claim 10 wherein the one or more operations further comprise modifying the first signal sequence or first modulation parameter of the first audio signal in response to processing the first sensor input or the second sensor input, according to at least one performance parameter.

14. The system of claim 10 wherein the one or more operations further comprise modifying the second signal sequence or second modulation parameter of the second audio signal in response to processing the first sensor input or the second sensor input, according to at least one performance parameter.

15. The system of claim 10 wherein the first modulation parameter or the second modulation parameter is a panning modulation comprising an audio navigation parameter.

16. The system of claim 10 wherein the one or more operations further comprise providing a feedback signal to the mobile electronic device in response to processing the first sensor input or the second sensor input.

17. The system of claim 10 wherein the first audio prompt is associated with an audio target discrimination task and the second audio prompt is associated with an audio navigation task.

18. The system of claim 10 wherein the at least one input parameter comprises a timing parameter and a task parameter.

19. The system of claim 10 wherein the two or more periodic time points comprise an instance of a cognitive training regimen.

20. A non-transitory computer-readable medium encoded with instructions for commanding one or more processors to execute operations of a method for audio-based cognitive training, the operations comprising:

processing a first audio signal and a second audio signal according to one or more audio processing parameters, the one or more audio processing parameters comprising at least one of a sequencing parameter and a modulation parameter, wherein the first audio signal comprises a first audio prompt and the second audio signal comprises a second audio prompt;

outputting each of the first audio signal and the second audio signal to an audio output device at two or more time points;

receiving a first sensor input in response to outputting the first audio signal at the two or more time points;

receiving a second sensor input in response to outputting the second audio signal at the two or more time points; and processing the first sensor input and the second sensor input according to at least one input parameter, wherein the first sensor input or the second sensor input comprises a motion sensor input in response to a listener turning an input device in a direction of the first audio signal or the second audio signal in a stereo field.

* * * * *